United States Patent
Kryzanski

(10) Patent No.: US 11,612,739 B2
(45) Date of Patent: *Mar. 28, 2023

(54) METHODS AND DEVICES FOR SUBDURAL ELECTRODE ARRAY PLACEMENT

(71) Applicant: Tufts Medical Center, Inc., Boston, MA (US)

(72) Inventor: James Kryzanski, Boston, MA (US)

(73) Assignee: Tufts Medical Center, Inc., Boston, MA (US)

( * ) Notice: Subject to any disclaimer, the term of this patent is extended or adjusted under 35 U.S.C. 154(b) by 783 days.

This patent is subject to a terminal disclaimer.

(21) Appl. No.: 16/586,354

(22) Filed: Sep. 27, 2019

(65) Prior Publication Data

US 2020/0094049 A1 Mar. 26, 2020

Related U.S. Application Data

(63) Continuation-in-part of application No. PCT/US2019/025580, filed on Apr. 3, 2019, which is
(Continued)

(51) Int. Cl.
*A61B 5/05* (2021.01)
*A61B 5/00* (2006.01)
(Continued)

(52) U.S. Cl.
CPC ............ *A61N 1/0531* (2013.01); *A61B 5/24* (2021.01); *A61B 5/4064* (2013.01);
(Continued)

(58) Field of Classification Search
None
See application file for complete search history.

(56) References Cited

U.S. PATENT DOCUMENTS

| 5,044,368 A | 9/1991 | Putz |
| 6,024,702 A | 2/2000 | Iversen |

(Continued)

FOREIGN PATENT DOCUMENTS

WO 2011084788 A2 7/2011

OTHER PUBLICATIONS

Dixi Medical, "Microdeep depth electrode." Retrieved from http://www.diximedical.com/en/microsdeep-depth-electrode on Apr. 9, 2018, 10 pages.
(Continued)

*Primary Examiner* — Jon Eric C Morales
(74) *Attorney, Agent, or Firm* — Occhiuti & Rohlicek LLP

(57) ABSTRACT

Disclosed are devices, electrodes, systems, methods, and other implementations, including a system that includes a subdural sound comprising an elongated structure configured to be placed within a subdural space of a brain area of a patient, and an electrode comprising an elongated body, a plurality of electrical contacts disposed on a substantially flat first side of the elongated body, and a soundage channel defined along a longitudinal axis of the electrode and open at opposite ends. The soundage channel at the leading end of the electrode is fitted on the trailing end of the elongated structure of the subdural sound so as to be advanced, when the subdural sound is placed within the subdural space, to a target site in the subdural space for tangential placement on target tissue in the subdural space of the brain area.

38 Claims, 14 Drawing Sheets

Related U.S. Application Data a continuation of application No. 15/948,625, filed on Apr. 9, 2018, now Pat. No. 10,912,937.

(51) Int. Cl.
*A61N 1/05* (2006.01)
*A61N 1/36* (2006.01)
*A61B 5/24* (2021.01)

(52) U.S. Cl.
CPC .......... *A61B 5/4094* (2013.01); *A61B 5/6868* (2013.01); *A61N 1/0529* (2013.01); *A61N 1/36064* (2013.01)

(56) References Cited

U.S. PATENT DOCUMENTS

| | | |
|---|---|---|
| 6,978,180 B2 | 12/2005 | Tadlock |
| 8,364,237 B2 | 1/2013 | Stone et al. |
| 9,820,668 B2 | 11/2017 | Hua |
| 2002/0022873 A1 | 2/2002 | Erickson et al. |
| 2003/0009207 A1 | 1/2003 | Paspa et al. |
| 2004/0122360 A1 | 6/2004 | Waldhauser et al. |
| 2005/0090885 A1 | 4/2005 | Harris et al. |
| 2005/0234507 A1 | 10/2005 | Geske et al. |
| 2010/0179518 A1 | 7/2010 | Ludvig et al. |
| 2010/0241100 A1 | 9/2010 | Blumenfeld et al. |
| 2016/0089515 A1 | 3/2016 | Hansen et al. |
| 2016/0256062 A1 | 9/2016 | Greger et al. |
| 2017/0007825 A1 | 1/2017 | Thakkar et al. |
| 2017/0173340 A1 | 6/2017 | Gupte et al. |

OTHER PUBLICATIONS

Greger, et al., "A chronically implantable, hybrid cannula-electrode device for assessing the effects of molecules on electrophysiological signals in freely behaving animals." J. Neurosci Methods. Jul. 30, 2007, 163(2): 321-325.

Du Hoffmann et al., "An inexpensive drivable cannulated microelectrode array for simultaneous unit recording and drug infusion in the same brain nucleus of behaving rats," J. Neurophysiol., Aug. 2011; 106(2): pp. 1054-1064.

Kaiboriboon et al., "Epilepsy surgery in the United States: Analysis of data from the National Association of Epilepsy Centers." Epilepsy Research 116 (2015) pp. 105-109.

Rolston et al., "Rate and Complications of Adult Epilepsy Surgery in North America: Analysis of Multiple Databases." Accepted Manuscript to Appeal in Epilepsy Research, Accepted date: May 5, 2016, 31 pages. http://dx.doi.org/10.1016/j.eplepsyres.2016.05.001.

International Search Report and Written Opinion, PCT Application No. PCT/US2020/052426, dated Jan. 19, 2021 (14 pages).

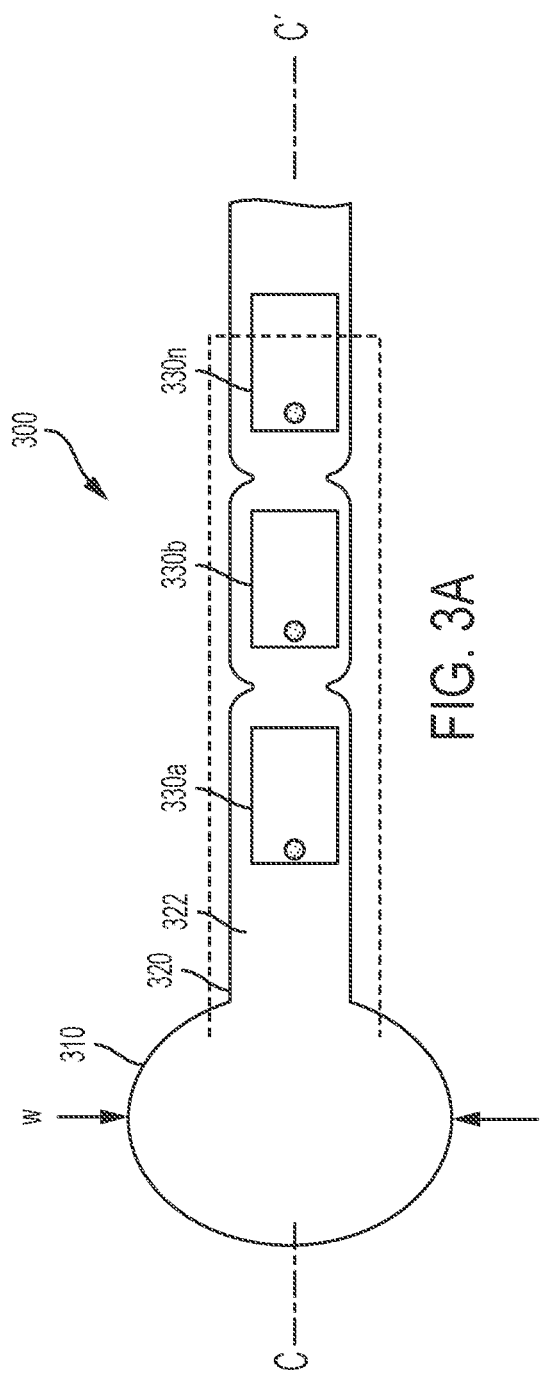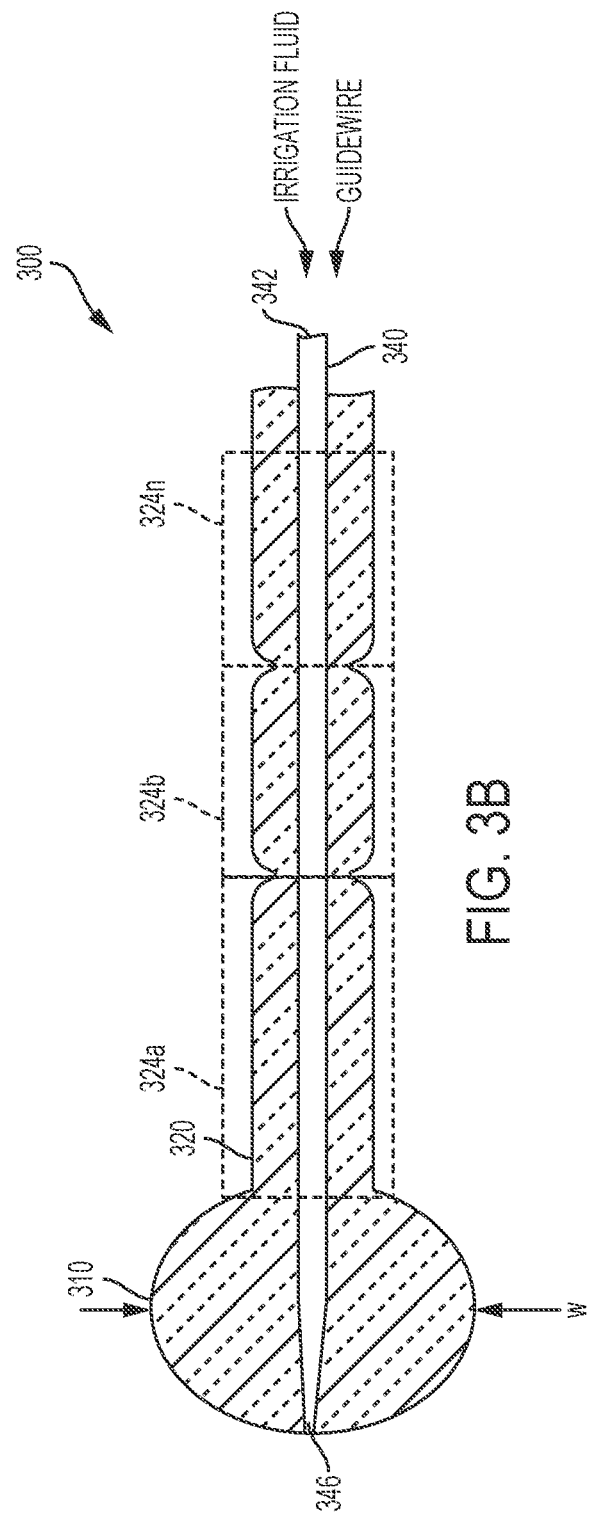

METHODS AND DEVICES FOR SUBDURAL ELECTRODE ARRAY PLACEMENT

RELATED APPLICATIONS

This application is a continuation-in-part (CIP) application of, and claims priority to, International Application No. PCT/US2019/025580, entitled "METHODS AND DEVICES FOR GUIDED SUBDURAL ELECTRODE ARRAY PLACEMENT," and filed Apr. 3, 2019, which is a continuation application, claiming the benefit of, and priority to, U.S. Non-Provisional application Ser. No. 15/948,625, filed Apr. 9, 2018, the contents of all of which are herein incorporated by reference in their entireties.

BACKGROUND

Epilepsy will affect 1 in 26 Americans over their lifetimes and in 30% of cases medications are not effective in controlling the seizures. In these 'medically refractory' cases, surgical options should be considered given the malignant nature of uncontrolled seizures. Recent studies have concluded that epilepsy surgery is underutilized. Nevertheless, surgical procedures for intracranial electrode placement are common and increasing. Furthermore, recent technological advances such as responsive neurostimulation with the Neuropace™ system provide potential surgical options for patients who have seizures coming from multiple or eloquent brain areas and were previously not candidates. These patients nearly always require initial subdural electrode monitoring. Subdural electrodes are also used in cyberprosthetic devices where surface electrode recordings are used to move paralyzed limbs in patients with neurologic injury. Additional applications where electrodes may be used include responsive neurostimulation to treat epilepsy and cortical stimulation for chronic pain. These applications often rely on conventional subdural grid technology.

The crucial aspect of surgical evaluation is identifying the area(s) of the brain responsible for seizures and often this is done by intracranial electrode placement. Subdural, or brain surface, electrodes are often used in patients with refractory epilepsy to determine the seizure focus. The subdural space is the area between the brain surface and the dura, or fibrous covering, of the brain. The 'ictal zone', or area of seizure onset, is determined by the electrodes covering the area. Therefore, surgeons try to cover a large area of the cortex with electrodes in order to maximize the chance of finding the ictal zone. The current technique for placing a subdural electrode array involves surgery to remove a significant piece of the skull and then lay a subdural grid and numerous strip electrodes on the brain surface. The invasiveness and risk of this procedure is considerable.

Another technique that is used for the placement of brain electrodes is based on using stereo-EEG, where electrodes are placed into the brain itself and not on the brain surface through small skull drill holes in computer-determined trajectories. Though superficially less invasive than subdural electrode arrays, this technique requires multiple penetrations of the brain and does not optimally record from the brain surface, where most seizures arise. Placement of subdural electrodes through small drill holes is currently challenging because it is difficult to advance the electrode into the subdural space due to the initial sharp angle maneuvering (often close to 90°) necessary to advance the electrode under the skull and onto the brain surface. With this constraint it is challenging to apply a force vector that is tangential to the brain surface, and consequently the placement of subdural electrodes through a small drill hole risks brain injury due to inadvertent penetration. In addition, the broad, flat design of existing electrodes leads to crowding of components in the drill hole, making placement of even a small number of strips difficult if not impossible. This results in relatively poor surface coverage. Therefore it is not currently possible to place a large subdural electrode array through a small skull drill hole.

SUMMARY

Disclosed are devices, systems, methods, and other implementations to place electrode arrays (e.g., of subdural electrodes) through a small drill hole in the skull using a guiding mechanism, such as molded and flexible catheters, to navigate the electrodes into position.

In alternative embodiments, a subdural sound (also referred to as a "subdural depth sound", a "subdural depth sounding instrument," a "guiding probe," a "subdural probe," and/or a "guiding device") is first placed within the subdural space in a patient's brain. Image data obtained, for example, via an optic fiber included with the subdural sound, can be used to move the sound within the subdural space to maneuver the sound to the desired target site. Alternatively, the location of the sound can be determined through external imaging apparatus (e.g., X-Ray, MRI apparatus) when the sound is properly fitted with, for example, radiopaque indicators. The subdural sound generally includes a distance determination mechanism (hence the name "depth sound"), e.g., implemented through the inclusion of markings, that indicate the length of sound within the patient's body. Based on the determined length of the sound body within the subdural space, an appropriately-sized electrode comprising a soundage channel, with an electrode length substantially matching the length of the sound/sound body within the patient's body, is selected. The soundage channel is then fitted (at a leading opening of the soundage channel) onto a trailing end of the subdural sound, and the soundage channel (and with it the rest of the electrode) is advanced (pushed manually or via a thrusting mechanism that may be powered or actuated by a motor) along the sound for tangential placement at the target site (where the leading end of the sound is located). Thus, in such embodiments, the subdural sound is utilized to determine the appropriate size of the electrode, and to serve as a rail fitted into the soundage channel to allow the electrode to be advanced into position.

The alternative embodiments (in which a subdural sound is first placed in the subdural space) remedy two main issues:
  a) the combined guiding device and electrode unit can sometimes have difficulty making the 90 degree turns required for placement through a small bone exposure and into the subdural space even with very flexible materials. This results in a risk of brain injury during placement.
  b) It is difficult to accurately predict the electrode length required as sometimes unexpected obstacles (veins, adhesions, etc.) will impede passage through the subdural space. Without knowing the required electrode length, it is necessary to pass several electrodes into the subdural space before a suitable electrode length is determined. This is suboptimal because every additional passage increases risk of injury to the brain.

In some of the embodiments described herein, a thin and flexible subdural sound can navigate 90 degree turns under the bone edge into the subdural space. Once the sound is advanced into position, it creates a stable platform over which to pass a flexible electrode. The risk of brain injury is greatly reduced since the guiding sound can keep the electrode tangential to the brain during placement. Since the resistance in the subdural space is minimal, the guiding device itself can have a softness and flexibility whereby it would be unlikely to penetrate the brain even if directed perpendicularly with reasonable force (it would curl at the tip instead of penetrating). The flatness of the guiding sound device described herein resists perpendicular movement so the device (unlike, for example, a tubular catheter), and generally travels only in the intended directions.

Additionally, the initial placement of a guiding device also solves the second issue mentioned above since the electrode length can be determined from markings provided on the sound, and the appropriate electrode can be selected without any unnecessary passes through the subdural space.

In some embodiments, a potential array uses such electrodes in a radial fashion, thus obtaining extensive cortical electrode coverage from a small exposure and burr hole in the skull. An unlimited number of potential array configurations are possible by varying the burr hole size, location, and the number/direction of electrodes.

Thus, in some variations, a device is provided that includes an electrode comprising an elongated body, a plurality of electrode contacts disposed on a first side of the elongated body, and a cannulation channel defined along a longitudinal axis of the electrode. The device further includes a guiding mechanism received within the cannulation channel, the guiding mechanism configured to guide the electrode for placement at a target area inside a body of a patient.

Embodiments of the device may include at least some of the features described in the present disclosure, including one or more of the following features.

The cannulation channel may be defined within the elongated body.

The device may further include a sleeve disposed on a second side of the elongated body of the electrode, with the cannulation channel being defined by the sleeve.

The second side of the elongated body may be opposite the first side.

The elongated body may include a chain of body sections, with at least some of the body sections include tapered ends along a longitudinal axis of each of the at least some of the body sections, and with each of the plurality of electrode contacts being disposed at a respective different one of the body sections.

The elongated body may include a leading tip with an average width larger than a maximum body width of a remainder of the elongated body.

The cannulation channel may terminate at a reinforced area of a leading tip of the elongated body such that the cannulation channel is configured to cause the elongated body to be pulled into place from the leading tip using the guiding mechanism.

The cannulation channel may be configured to receive irrigation fluids dispensed through a perforated end located near a leading tip of the elongated body.

The device may further include an adapter fitted at an operator-end of the guiding mechanism, the adapter configured to at least direct the irrigation fluids from a fluid source for delivery via the cannulation channel. The adapter may include a luer-lock.

The guiding mechanism may include a guidewire defining an internal channel between the guidewire and internal walls defining the cannulation channel, with the internal channel being configured to receive irrigation fluids dispensed through a perforated end located near a leading tip of the elongated body.

The electrode may further include a radiopaque identifier element disposed proximate a leading tip of the elongated body.

The elongated body may include an elongated silicon-based elastomer body.

Each of the plurality of electrode contacts may include one or more of, for example, a stainless-steel contact and/or a platinum contact.

The electrode may include multiple folded electrode strips defining the elongated body, with the multiple folded electrode strip configured to be unfolded for deployment over the target area inside the body of the patient.

The target area may be a brain of the patient.

In some variations, an electrode is provided that includes an elongated body, a plurality of electrode contacts disposed on a first side of the elongated body, and a cannulation channel defined along a longitudinal axis of the elongated body. The cannulation channel is configured to receive a guiding mechanism to guide the electrode for placement at a target area inside a body of the patient.

Embodiments of the electrode may include at least some of the features described in the present disclosure, including at least some of the features described above in relation to the device, as well as one or more of the following features.

The cannulation channel may be defined within one of, for example, the elongated body, or a sleeve disposed on a second side of the elongated body.

The elongated body may include a chain of body sections, with at least some of the body sections including tapered ends along a longitudinal axis of each of the at least some of the body sections, and with each of the plurality of electrode contacts being disposed at a respective different one of the body sections.

The elongated body may include a leading tip with an average width larger than a maximum body width of a remainder of the elongated body.

The electrode may further include multiple folded electrode strips defining the elongated body, the multiple folded electrode strips configured to be unfolded for deployment over the target area inside the body of the patient.

In some variations, a method is provided that includes forming a hole to access an internal target area inside a body of a patient, coupling a guiding mechanism to an electrode comprising an elongated body and a plurality of electrode contacts disposed on a first side of the elongated body, and guiding the electrode, using the guiding mechanism, through the hole for placement at the target area inside the body of the patient.

Embodiments of the method may include at least some of the features described in the present disclosure, including at least some of the features described above in relation to the device and the electrode, as well as one or more of the following features.

Coupling the guiding mechanism to the electrode may include inserting the guiding mechanism through a cannulation channel defined along a longitudinal axis of the elongated body of the electrode.

Inserting the guiding mechanism through the cannulation channel may include one of, for example, inserting the guiding mechanism to the cannulation channel defined within the elongated body, or inserting the guiding mechanism to the cannulation channel defined in a sleeve disposed on a second side of the elongated body.

The method may further include subsequent to placement of the electrode, repeating the coupling and guiding for one or more other electrodes for placement of the one or more other electrode at respective locations.

Guiding the electrode may further include delivering irrigation fluid via the cannulation channel, the irrigation fluids being dispensed through one or more irrigation openings in the elongated body.

The electrode may include multiple folded electrode strips defining the elongated body, and the method may further include unfolding the multiple folded electrode strips defining the elongated body to deploy the unfolded electrode strips over the target area inside the body of the patient.

In some variations, a system is provided that includes a subdural sound comprising an elongated structure configured to be placed within a subdural space of a brain area of a patient, and an electrode comprising an elongated body, a plurality of electrical contacts disposed on a substantially flat first side of the elongated body, and a soundage channel defined along a longitudinal axis of the electrode and open at opposite ends. The soundage channel at the leading end of the electrode is fitted on the trailing end of the elongated structure of the subdural sound so as to be advanced, when the subdural sound is placed within the subdural space, to a target site in the subdural space for tangential placement on target tissue in the subdural space of the brain area.

Embodiments of the system may include at least some of the features described in the present disclosure, including at least some of the features described above in relation to the device, the electrode, and the method, as well as one or more of the following features.

The subdural sound may include the elongated structure with at least one substantially flat surface.

The sound may have a substantially rectangular cross section at points along a longitudinal axis of the elongated structure of the subdural sound.

The soundage channel of the electrode may define an inner channel space, with a substantially rectangular cross section, to be snugly fitted on the elongated structure of the subdural sound having the substantially rectangular cross section.

The subdural sound may further include a distance determination mechanism configured to indicate penetration distance of the subdural sound into the subdural space.

The distance determination mechanism may include a plurality of markings disposed along the elongated structure to indicate the penetration distance of the subdural sound.

The plurality of markings may include radiopaque markings.

The elongated structure of the subdural sound may include a body with stiffness gradient such that a leading end of the elongated structure is more flexible than at least another portion of the body.

The elongated structure of the subdural sound may include an elongated sound body with stiffness characteristics that restrict transverse deflection of the body along a transverse axis of the elongated sound body, the stiffness characteristics of the elongated sound body further configured to allow partial deflection along a normal axis that is normal to the transverse axis and a longitudinal axis of the elongated sound body.

The soundage channel may be defined within the elongated body of the electrode.

The system may further include a sleeve disposed on a second side of the elongated body of the electrode, with the soundage channel being defined by the sleeve.

The elongated body of the electrode may include a chain of body sections, with at least some of the body sections including tapered ends along a longitudinal axis of each of the at least some of the body sections, and with each of the plurality of electrical contacts being disposed at a respective different one of the body sections.

The elongated structure of the subdural sound may include a lubricious elongated sound body, and the electrode soundage channel fitted on the trailing end of the elongated structure of the subdural sound may be configured to be advanced towards a leading end of the elongated structure of the subdural sound by sliding along the lubricious elongated sound body of the subdural sound.

The system may further include an adapter fitted at one of an operator-end of the subdural sound or a trailing opening of the soundage channel, the adapter configured to at least direct irrigation fluids from a fluid source for delivery via the soundage channel.

Each of the plurality of electrical contacts may include one or more of, for example, a stainless-steel contact and/or a platinum contact.

The electrode may include multiple folded electrode strips defining the elongated body, the multiple folded electrode strip configured to be unfolded for deployment over the target tissue in the subdural space.

The sound may further include an irrigation channel, different from the soundage channel, configured to receive irrigation fluids dispensed through a perforated end located near a leading tip of the elongated structure of the electrode.

In some variations, an additional method is provided that includes forming a hole to access target tissue in a subdural space in a brain area of a patient, directing a subdural sound comprising an elongated structure through the hole to displace a leading end of the elongated structure of the subdural sound to a target site within the subdural space, and fitting a soundage channel of an electrode on a trailing end of the elongated structure of the subdural sound, with the soundage channel defined along a longitudinal axis of the electrode. The electrode further includes an elongated body and a plurality of electrical contacts disposed on a substantially flat first side of the elongated body, the soundage channel being open at opposite ends of the electrode. The method additionally includes advancing the electrode towards the leading end of the subdural sound for placement tangential to the target tissue in the subdural space of the patient.

Embodiments of the additional method may include at least some of the features described in the present disclosure, including at least some of the features described above in relation to the device, the electrode, the first method, and the system, as well as one or more of the following features.

The subdural sound may include an elongated structure with at least one substantially flat surface, and having a substantially rectangular cross section at points along a longitudinal axis of the elongated structure of the subdural sound.

The soundage channel may define an inner channel space with a substantially rectangular cross section. Fitting the soundage channel on the trailing end of the elongated structure of the subdural sound may include snugly fitting the soundage channel, with the substantially rectangular cross section, on the elongated structure of the subdural sound with the substantially rectangular cross section.

The subdural sound may further include a distance determination mechanism configured to indicate a penetration distance of the subdural sound into the subdural space.

Fitting the soundage channel on the trailing end of the elongated structure of the subdural sound may include determining penetration distance of the subdural sound into the subdural space based on markings disposed on the elongated structure of the subdural sound, and fitting one of a plurality of available electrodes with a length selected based on the determined penetration distance.

The elongated structure of the subdural sound may include an elongated sound body with stiffness characteristics that restrict transverse deflection of the elongated sound body along a transverse axis of the elongated sound body, the stiffness characteristics of the elongated sound body further configured to allow partial deflection along a normal axis that is normal to the transverse axis and a longitudinal axis of the elongated sound body.

Fitting the soundage channel on the trailing end of the elongated structure of the subdural sound may include fitting the trailing end of the elongated structure of the subdural sound within the soundage channel defined in the elongated body of the electrode, or fitting the trailing end of the elongated structure of the subdural sound within the soundage channel defined in a sleeve disposed on a second side of the elongated body of the electrode.

The method may further include withdrawing, subsequent to placement of the electrode, the subdural sound, and repeating the directing, fitting, and advancing for one or more other subdural sounds and for one or more electrodes, at respective one or more locations in the subdural space.

The method may further include delivering irrigation fluid via the soundage channel.

The method may further include delivering irrigation fluid via an irrigation channel, different from the soundage channel, configured to receive irrigation fluids dispensed through a perforated end of the irrigation channel located near a leading tip of the elongated structure of the electrode.

The electrode may include multiple folded electrode strips defining the elongated body, and the method may further include unfolding the multiple folded electrode strips defining the elongated body to deploy the unfolded electrode strips over the target tissue.

In some variations, an additional electrode is provided that includes an elongated body, a plurality of electrode contacts disposed on a substantially flat first side of the elongated body, and a soundage channel defined along a longitudinal axis of the elongated body and open at opposite ends, the soundage channel configured to be fitted on a trailing end of an elongated structure of a subdural sound (configured to be placed within a subdural space of a brain area of a patient), in order to advance the electrode for tangential placement on target tissue in the subdural space.

Embodiments of the additional electrode may include at least some of the features described in the present disclosure, including at least some of the features described above in relation to the device, the first electrode, the methods, and the system, as well as one or more of the following features.

The soundage channel may be defined within one of, for example, the elongated body, or a sleeve disposed on a second side of the elongated body of the electrode.

The soundage channel may define a substantially rectangular cross section, at points along a longitudinal axis of the soundage channel, snugly fittable on a trailing end of the elongated structure of the subdural sound having a corresponding substantially rectangular cross section at points along a longitudinal axis of the elongated structure of the subdural sound, when the elongated structure of the subdural sound is placed within the subdural space of the patient.

Other features and advantages of the invention are apparent from the following description, and from the claims.

BRIEF DESCRIPTION OF THE DRAWINGS

These and other aspects will now be described in detail with reference to the following drawings.

FIG. 3A is a diagram of an inferior surface of a cannulated subdural electrode with electrode contacts.

FIG. 3B is a width-wise cross-sectional diagram of the cannulated subdural electrode of FIG. 3A.

Like reference symbols in the various drawings indicate like elements.

DESCRIPTION

Figure 1:
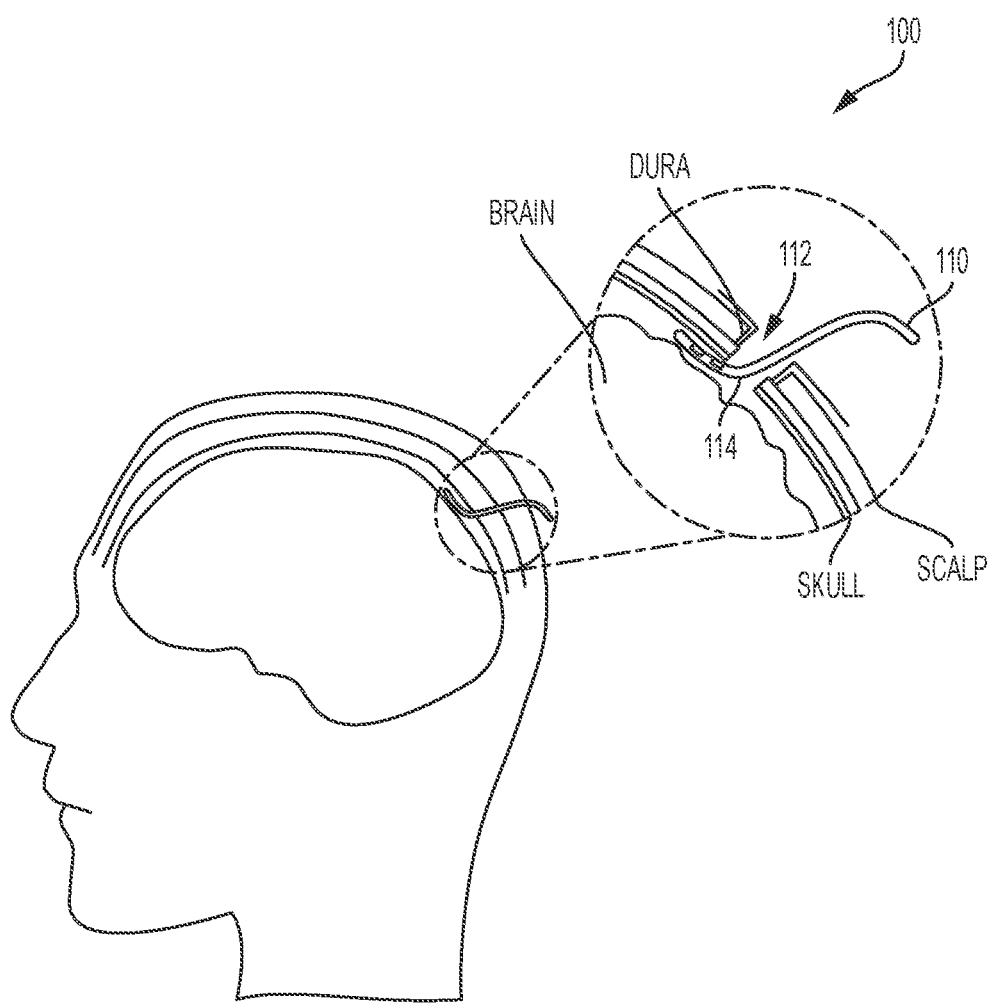
FIG. 1 is a diagram of a subdural electrode placement procedure performed through minimal bone exposure.

Disclosed herein are methods, systems, devices, and other implementations to place a subdural electrode array through a small drill hole in the skull using a guide mechanism, such as molded and flexible catheters, to navigate the electrodes into position. The implementations described herein include a device that includes an electrode comprising an elongated body, a plurality of electrode contacts (i.e., electrical contacts) disposed on a first side of the elongated body, and a cannulation channel defined along a longitudinal axis of the electrode, and a guiding mechanism received within the cannulation channel, with the guiding mechanism configured to guide the electrode for placement at a target area inside a body of a patient. The implementations also include an electrode comprising an elongated body, a plurality of electrode contacts disposed on a first side of the elongated body, and a cannulation channel defined along a longitudinal axis of the elongated body, the cannulation channel configured to receive a guiding mechanism to guide the electrode for placement at a target area inside a body of the patient. The implementations described herein further include a method including forming a hole to access an internal target area inside a body of a patient, coupling a guiding mechanism to an electrode comprising an elongated body and a plurality of electrode contacts disposed on a first side of the elongated body, and guiding the electrode, using the guiding mechanism, through the hole for placement at the target area inside the body of the patient.

In the above example embodiments, an electrode and a moldable guide or catheter are generally placed simultaneously in the patient's body, and the guide or catheter is then removed. This can create some technical challenges. Firstly, it is difficult to determine the optimal length of the electrode prior to placement. Secondly, there is increased stiffness of the electrode/catheter combined assembly that makes the necessary initial 90 degree turn difficult. Accordingly, to remedy these difficulties, in some example embodiments, a lubricious, flexible, guiding device is first placed intro the subdural space through a small skull burr hole and the channeled electrode is then placed over the guiding device and advanced into the desired position in the subdural space. The guiding device (also referred to as a "subdural sound" or "subdural depth sound") is then removed and may be used to place additional electrodes. In such implementations, the proper length electrode can be selected based on the inserted length of the sound. Furthermore, first deploying the sound (prior to advancing the electrode on the deployed sound) can help stabilize the system, and make it simpler to negotiate sharp (e.g., 90 degree turns) by first placing the sound in the subdural space prior to advancing the electrode on the already deployed sound. In such embodiments, the electrode structure is configured such that the channel of the sound device (referred to as a "subdural sound") is open at the both ends (in the combined assembly embodiments, the soundage channel may be open at both ends, but does not need to be). In some example implementations, the sound has a substantially rectangular cross-section that can be fitted into a soundage channel (of the electrode) with complementary substantially rectangular cross-section, thus allowing for a snug fit between the sound and soundage channel (which can lower the risk of contamination, and establish sufficient traction to advance the soundage channel along the sound). Optionally, in some examples, the channeled subdural electrode may include strips or grids that could unfold or spread out in the subdural space. The subdural sound may optionally be fitted with optical, electrical, or chemical sensors that confirm location in the subdural space during passage. Additional optional features may include implementations where the electrode arrays are used for uses other than epilepsy, including for cortical stimulators and cyberprostheses. In these situations the electrodes are placed as part of a permanent prosthesis and not just for temporary monitoring. It is to be noted that in some situations, inserting the combined assembly of an electrode and a guide/sound instrument (i.e., inserting them simultaneously) may be advantageous, for example, when it desired to save on time and potential injury to the tissue, traversing the combined assembly may be preferred.

FIG. 1 is a diagram 100 illustrating subdural electrode placement procedure performed through minimal bone exposure (burr-hole craniectomy). As illustrated, in order to achieve such minimal bone exposure, electrodes to be deployed on brain tissue (such as the schematically depicted flexible electrode 110) have to navigate acute angled paths/trajectories in order to allow placement of such an electrode tangential to the brain surface. For example, once an opening or hole 112 is formed, the electrode array 110 is configured to be bent so that its elongated body defines an acute angle (at a location 114 on the electrode 110, in the example of FIG. 1), which may be 70-90°). The structure of the electrode used may be configured to be bent to form angled sections over any angular range.

As will be described in greater detail below, the implementations described herein include use of cannulated subdural electrodes. Cannulation allows for guidance by, for example, a molded introducer catheter. The catheter allows for irrigation at the tip of the electrode to lubricate its passage. The moldable nature of catheters will allow for navigation of the electrode around the angles that currently limit electrode placement. Alternate embodiments include any catheter guided or cannulated subdural electrode, including strips or grids that could unfold or spread out in the subdural space. Alternate embodiments also include subdural electrodes used for uses other than epilepsy, including cortical stimulators and cyberprostheses. In those situations, the electrodes may be placed as part of a permanent prosthesis and not just for temporary monitoring. The electrodes described herein, and the procedures, systems, and apparatus for placing such electrodes, may also be used for other medical conditions in relation to other organs or parts of the body.

In some implementations, the electrode may be constructed from silastic® (a product of Dow Corning Corporation, Midland, Mich.) with stainless steel contacts or platinum contacts. The leading tip of the electrode is generally broad to prevent twisting during insertion. The body of the electrode may taper (e.g., to a width of 3 mm) so as to allow placement of multiple (8 or more) electrodes through a small drill-hole. As will be discussed in greater detail below, a cannulation channel runs along the back side (noncontact side) of the electrode that can accommodate a catheter ranging, for example, from 3-5 French in size (1-1.67 mm outer diameter). The end of the cannulation channel at the tip of the electrode has a small channel that can direct irrigation from the cannulation to the electrode tip surface. The width of the electrode may be tapered between contacts in order to increase flexibility.

Figure 2A:
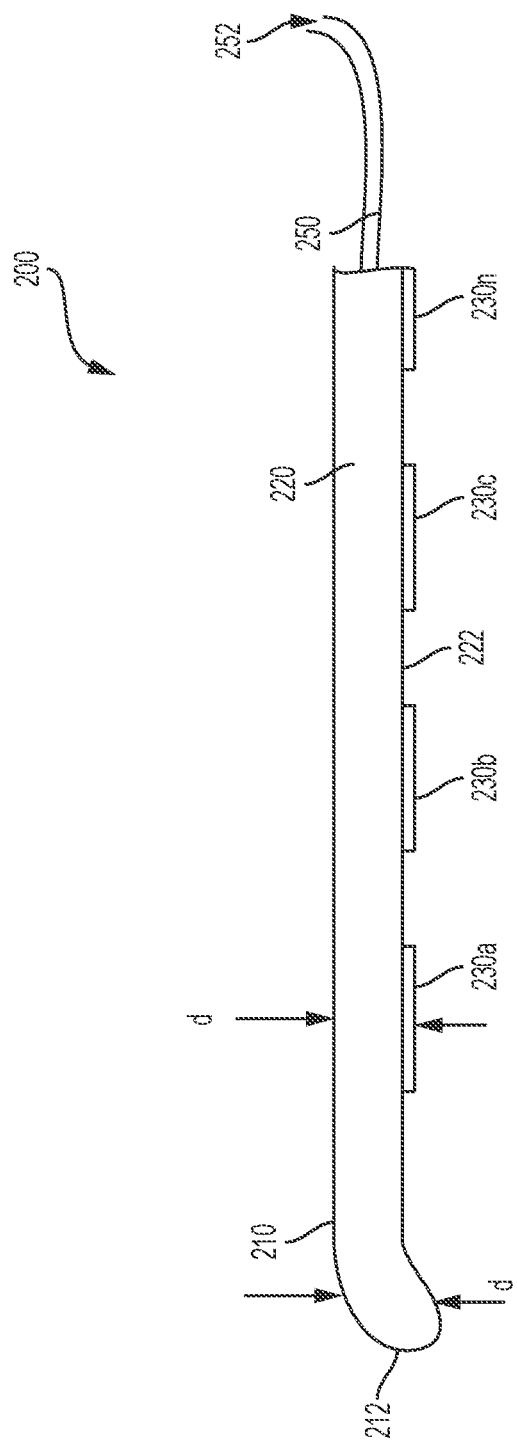
FIG. 2A is a side-view diagram of a cannulated subdural electrode that includes a guidewire/catheter entry point, and brain surface electrode contacts.

More particularly, with reference next to FIG. 2A, a diagram of a side view of a device 200 to facilitate deployment of electrodes within interior spaces inside a person's body, such as within a subdural space of a person, is shown. The device 200 includes an electrode 210 comprising an elongated body 220, with a plurality of electrode contacts 230*a-n* disposed on a first side 222 of the elongated body 220 (e.g., with n being 2, 3, 4, 8, or any other number of electrodes; generally, the number of contacts varies between 4-12). In some embodiments, the electrode may have only one (1) electrode contact. In some embodiments, the elongated body may be substantially flat (e.g., a strip-like structure), with a thickness, d, of dimensions 1-2 mm. Extending from each of electrodes 230*a-n* is a respective one of electrical wires 232*a-n* (shown in FIG. 2B) that can carry measured signals (representative of electrical activity within a brain, or of some other physiological activity with a target area where the electrode is deployed), and may also deliver electrical signal from an electrical source (e.g. a controller in communication with the various electrodes) to control the electrodes or to deliver electrical stimulation to the target area. In some embodiments, electrical signals may be communicated to and from the electrodes via a wireless interface (e.g., a UHF-based transceiver, such as UHF transceivers implemented in passive RFID devices, to allow electrical operation of the devices using power harvested from wireless signals; such wireless transceivers may be configured to operate in other RF bands). In such embodiments, wired electrical connections, such as the wired connections realized using the electrical wires 232a-n, may not be needed. In some examples, the electrodes 230a-n may be rectangular electrodes (or other electrode types and geometries) with dimensions, for example, of approximately 2.75 mm×4.57 mm (such dimensions can be used as to provide approximately the same contact area as a 4 mm round electrode, but the rectangular contact will have a narrower profile). The contacts may be spaced every 10 mm, or some other appropriate distance. The number of contacts per electrode can vary from 4 up to 12 and possibly more. The wire extending from an electrode is as small as possible (1.1 mm) The wires may have unique color codes, and may also include radio-opaque unique identifiers that allow for identification on x-ray.

Figure 2B:
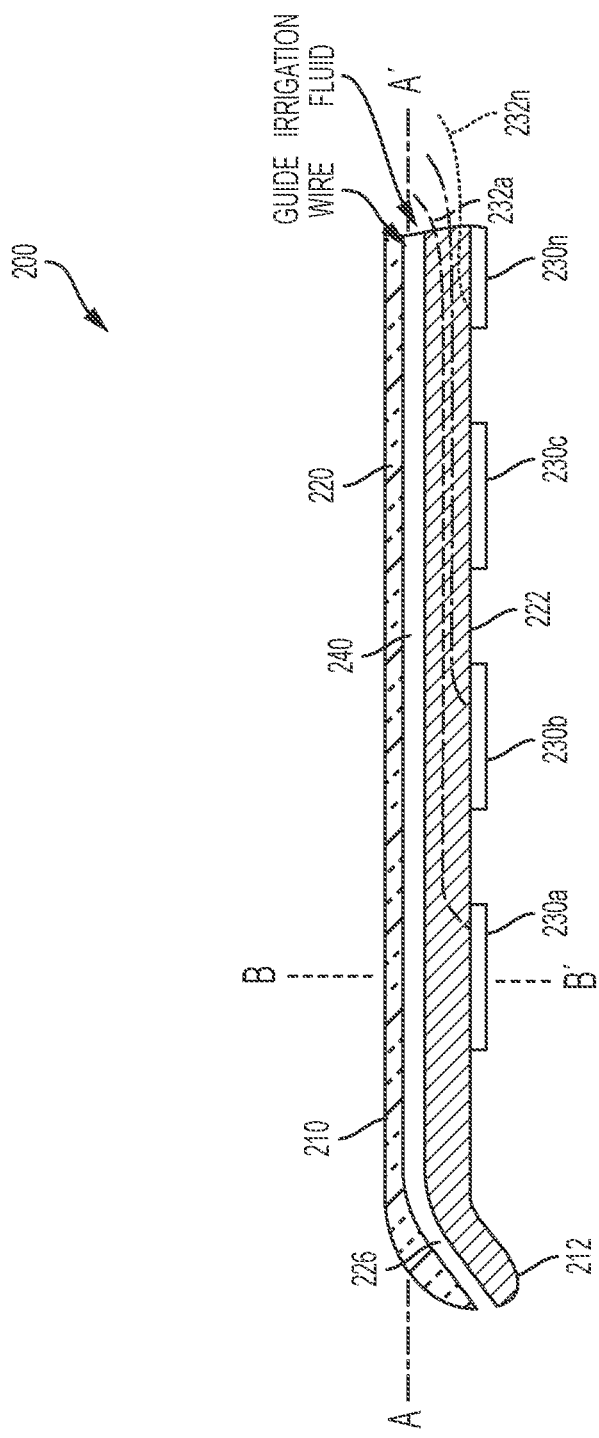
FIG. 2B is a lengthwise cross-section diagram of the cannulated subdural electrode of FIG. 2A.

As shown with further reference to FIG. 2B, providing a lengthwise cross-section diagram of the cannulated subdural electrode of FIG. 2A, the electrode 210 further includes a cannulation channel 240 defined along a longitudinal axis of the electrode 210. In the example implementations of FIGS. 2A and 2B, the cannulation channel 240 is defined within the elongated body 220, e.g., the elongated body 220 includes an internal channel that is contained within the elongated body 220. However, in some embodiments, the cannulation channel may be provided as the internal channel of a sleeve that is disposed as a different part on a second side (opposite the first side 222 on which the electrodes 230a-n are disposed) of the elongated body 220 (the sleeve, not shown in FIGS. 2A or 2B, may extend integrally from the elongated body 220, or may be coupled in some manner to the elongated body 220). The cannulation channel 240, be it a cannulation channel defined within the elongated body 220 or a channel defined within a separate sleeve, is configured to receive a guiding mechanism 250, such as a catheter, a guidewire, or any other actuatable mechanism configured to be fitted inside the cannulation channel 240 to guide the electrode 210 for placement at a target area inside a body of a patient, and to be withdrawn upon deployment of the electrode at the target. In some variations, the cannulation channel may terminate at a reinforced area of a leading tip 212 of the elongated body 220, with the reinforced area configured to facilitate causing the elongated body to be pulled into place from the leading tip using a guidewire or a catheter.

In some embodiments, the elongated body 220 (and/or a sleeve coupled thereto) may be made from a flexible material, such as a plastic polymer (e.g., polyurethane), elastomers (e.g., silicone elastomers such as silastic®), etc. The elongated body 220 of the electrode 210 (and/or a cannulation sleeve that may be attached thereto in some embodiments) may be produced via, for example, an extrusion process, or a molding process (with the resultant structure comprising the internal space defining the cannulation channel). Upon formation of the elongated body structure, electrical contacts, such as the electrical contacts 230a-n, may be placed on one side of the elongated body. In embodiments in which a cannulation sleeve is disposed on a second side of the elongated body, the elongated body and the cannulation sleeve may be produced as separate parts that are then attached to each other (through a bonding process, such as gluing, thermal bonding, etc.)

As noted, the device 200 further includes a guiding mechanism, such as the guiding mechanism 250 depicted in FIG. 2A, which may include a catheter or some other guiding mechanism (e.g., guidewire). The guiding mechanism is configured to be received within a cannulation channel, such as the cannulation channel 240 depicted in FIG. 2B, when an electrode (e.g., 210) is to be placed within a target area inside a body of a patient. In some implementations, the guidewire or catheter may be constructed from silastic®, have a size of 3-5 French gauge, and be approximately 20 cm in length. The operator end of the guiding mechanism terminates in an adapter, such as luer-lock, that allows use of a syringe to both irrigate and rotate the catheter if necessary. A separate controlling instrument may be coupled to the operator end of the guiding mechanism, and may be configured to be controlled so as to actuate the leading end of the catheter to control its movement (i.e., to change its direction so as to negotiate sharp corners and change its trajectory en route to the destination location for the electrode). Examples of catheters that may be used in conjunction with the implementations described herein include the Stryker Excelsior catheters. Other types of catheters may also be used. In some examples, about 10 mm of the catheter tip may be firm and molded into an angle appropriate to facilitate passing the electrode over the surface of the target area (e.g., the brain) through a small drill hole. The remainder of the guiding mechanism (e.g., catheter) may be flexible. The guiding mechanism may be constructed from a radiopaque material (such as radiopaque polyurethane) that is visible through various radio imaging technologies (e.g., x-rays) in order to determine the location of the guiding mechanism within a body of a patient. In some implementations, the guiding mechanism (be it a catheter, guidewire, or some other type guide mechanism) may be equipped with one or more fiber optical wires that attach to a light-capture device (e.g., camera). A light source may deliver light signals via one such optical fiber, whose end is located near the leading end of the catheter, to illuminate the area through which the catheter (and thus the electrode) is advancing, while another fiber optical wire may deliver reflected light back to the light-capture device, via a lens assembly, to allow the operator to view the area where the electrode is located. In some embodiments, the optical fibers may be separately fitted through the cannulation channel rather than being part of the catheter device or assembly.

Figure 5:
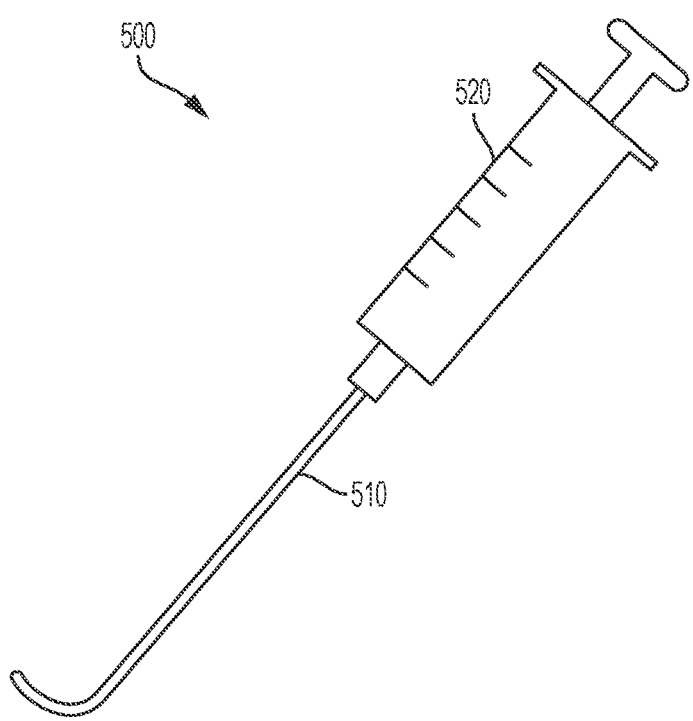
FIG. 5 is a schematic diagram of an implementation comprising a catheter and a syringe to introduce irrigation fluid into an inner channel defined in the catheter.

In embodiments in which the guiding mechanism comprises a catheter, such a catheter may be a tube that defines an internal channel through which irrigation fluid can pass and be delivered to irrigate the area surrounding the progressing structure (e.g., the electrode 210 of FIGS. 2A and 2B). For example, and as illustrated in FIG. 2B, an irrigation channel 226 may be defined at a distal end of the elongated body 220. Irrigation fluid introduced into the inner channel of the catheter can exit at one or more perforations or openings located at an end of the catheter that is placed near the elongated body's distal end (by passing the catheter through the cannulation channel 240). In the example of FIG. 2A, the catheter or guidewire is shown to have a distal opening 252 through which irrigation fluid (introduced, for example, using a syringe), may pass, and exit via the irrigation channel 226 to the area around the electrode. For example, FIG. 5 is a schematic diagram of an implementation 500 comprising a catheter 510 (which may be similar to the catheter 250 of FIG. 2A) and a syringe 520 to introduce irrigation fluid into an inner channel in the catheter. The catheter 510 is configured to be received in a cannulation channel (such as the cannulation channel 240 of FIG. 2B) during electrode placement. The catheter/guidewire may be implemented with an angled tip to allow the catheter, and thus the electrode, to navigate the acute angled paths illustrated, for example, in FIG. 1. The syringe 520 allows for irrigation to be directed through the cannulation channel, and out at the electrode tip (e.g., via the cannulation channel 226 of FIG. 2B), thus lubricating the surface of the target area (e.g., brain), and the path thereto, during placement of the electrode. In some embodiments, a multi-perforated catheter may be used that includes multiple perforations (e.g., located at a distal/leading tip of the catheter) to irrigate the areas through which the electrode (e.g., the array 210 of FIG. 2) passes. Irrigations fluids may thus flow (under pressure delivered by an external syringe or pump) through the irrigation perforation(s), and then through channels or perforations defined between the cannulation channel (e.g., the channel 240) and extending to the side of the elongated body on which the electrical contacts (e.g., 230a-n) are disposed.

Figure 6:
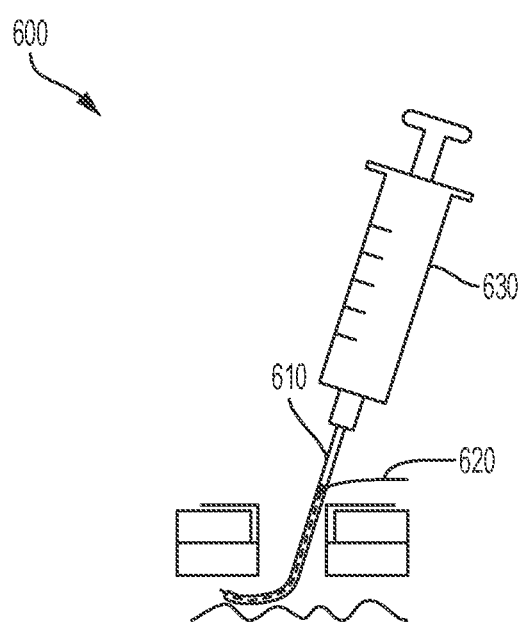
FIG. 6 is a schematic diagram illustrating electrode placement procedure using an angled-tip catheter.

FIG. 6 is a diagram of another example implementation of a system 600 for placing electrodes in the subdural space. In this example, the guiding mechanism used is a specially designed angled-tip catheter 610 that facilitates navigating an electrode at an acute angle under the skull edge. As shown in FIG. 6, the angled-tip catheter is coupled to an electrode 620 by, for example, inserting the leading end of the angled-tip catheter 610 (the leading end may have a single or multiple irrigation perforations) into the cannulation channel of the electrode. Irrigation fluid may be introduced into an internal channel in the catheter 610 using a syringe 630 that is coupled to the opening of the catheter 610 via an adapter (not shown) such as a luer-lock.

In various examples, the guiding mechanism may not have its own internal channel, and instead, irrigation fluid may flow in a channel defined between the body of the guiding mechanism (e.g., guidewire) and the interior walls of the cannulation channel. Here too, the irrigation fluid may exit the cannulation channel through one or more perforations or openings in the cannulation channel, and be directed to the area to be irrigated via irrigation channels defined in the elongated body 220, including the irrigation channel 226 depicted in FIG. 2B.

With reference next to FIG. 3A, a diagram showing a bottom view of a cannulated subdural electrode 300, which may be similar to the electrode 210 of FIGS. 2A-B, is provided. The electrode 300 comprises a plurality of electrical contacts 330a-n disposed on a surface 322 (e.g., the tissue-facing surface, also referred to as the contact surface) of an elongated body 320 (which may be similar to the elongated body 220). As also discussed in relation to the electrode 210 of FIGS. 2A-B, here too, the electrical contacts 330a-n may be rectangular electrodes (or other electrode types and geometries) with dimensions, for example, of approximately 2.75 mm×4.57 mm. The contacts may be disposed on the surface 322 at uniform spacing from each other (e.g., spaced every 10 mm) The number of contacts per electrode can vary from 4 up to 12, and may possibly be outside this range. Each of the electrical contacts may be identifiable through using a radio-opaque identifier (so that it can be easily recognized using different imaging technologies such as x-ray imaging, CAT imaging, etc.) Such identifiers may be numbered identifiers, or other alphanumerical identifiers. In embodiments in which the electrical contacts are connected to a central controller (such as the controller 920 illustrated in FIG. 9), configured to receive and process measurements performed by the electrical contacts or to send electrical signals to the electrical contacts, the wires used may have a gauge of, for example, 1.1 mm. The wires may have unique color codes (to facilitate placement of the electrodes and wiring). As noted, in some embodiments, the electrical contacts may include wireless communication circuitry adapted to establish wireless communication with the central controller through which identification information and electrical signaling may be communicated.

As further shown in FIG. 3A, and with reference also to FIG. 3B, providing a width-wise cross-sectional diagram of the cannulated subdural electrode 300 of FIG. 3A, the electrode 300 includes a distal (leading) tip 310 with an average width larger than a maximum body width of a remainder of the elongated body 320. In the examples of FIGS. 3A-B, the minimum width of the leading tip 310 is greater than the maximum width of the rest of the elongated body 320 of the electrode 300 (the maximum width of the leading tip is denoted using the arrow marking a width, W, at around the half-way point of the tip 310). The larger width of the leading tip (in some embodiments, the leading tip may be significant wider than the remainder part of the elongated body) allow the electrode to resist/reduce twisting or folding during placement of the electrode. In some embodiments, a radiopaque identifier element may be disposed proximate to the leading tip 310 of the elongated body to allow tracking of the location of the electrode while it is being maneuvered to its destination location. As illustrated in FIGS. 3A-B, in some implementations, the electrode 300 is tapered between contacts to increase flexibility. Thus, in such embodiments, the elongated body 320 may include a chain of body sections 324a-n, with at least some of the body sections including tapered ends along a longitudinal axis of electrode, and with each of the plurality of electrodes being disposed at a respective different one of the body sections 324a-n.

As additionally shown in FIG. 3B, a cannulation channel 340, which may be similarly structured to the cannulation channel 240 of FIGS. 2A-B, is defined within the elongated body 320 of the electrode 300. The cannulation channel 340 is configured to receive a guiding mechanism (a catheter or guidewire) that is placed via an entry opening 342 of the electrode 300, and can be pushed substantially to the leading tip 310 of the electrode 300. As with the electrode 210 of FIGS. 2A-B, irrigation fluid can be delivered via an internal channel in the catheter or guidewire, or via through the space defined between the internal walls of the cannulation channel 340 and the exterior of the catheter/guidewire received within the cannulation channel 340. In some implementations, the cannulation channel 340 may be tapered at the tip to allow passage of irrigation fluid while confining the catheter or guidewire (e.g., the catheter or guidewire may have a diameter larger than the diameter of the distal opening 346 of the cannulation channel 340 located at around the leading tip 310).

As noted herein, in some embodiments, the elongated body of an electrode may taper (e.g., to a width of 3 mm) in order to allow placement of multiple electrodes (to form an electrode array) through a single drill hole formed in the skull (or some other area of the body of the patient). To further facilitate deployment of multiple electrodes through a single drill hole, in some implementation, an electrode inserted through a drill hole may comprises multiple folded electrode strips that define the elongated body. The multiple folded electrode strips are configured to be unfolded for deployment over a target area within the body. Thus, a guiding mechanism may be fitted within a cannulation channel defined for such a folded electrode (the folded electrode may be associated with a single cannulation channel, rather than have individual cannulation channel for each of the folded electrode strips). Upon reaching the destination location (through actuation of the guiding mechanism to navigate the folded electrode), the guiding mechanism may further be configured to be actuated so as to cause the unfolding of the individual folded electrode strips (e.g., by releasing a latch that maintains the electrodes in a folded array, and then causing a rolling motion to unspool or unfold the electrode strips). As also noted herein, target areas where the electrodes described herein may be deployed may include, in addition to a patient's brain, other hard to reach areas of the body (e.g., the gastrointestinal system). Furthermore, the electrodes described herein may also be used as cortical stimulators and cyberprostheses. In these situations, the electrodes may be placed as part of a permanent prosthesis and not just for temporary monitoring and/or stimulation.

Figure 4B:
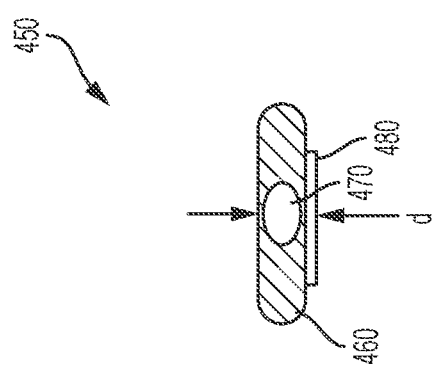
FIG. 4B is a transverse cross-sectional diagram of a body of an electrode.
Figure 4A:
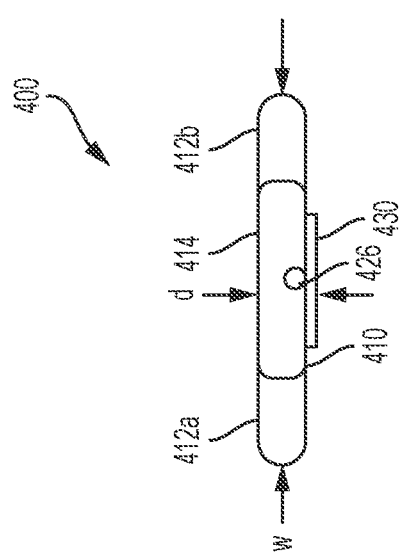
FIG. 4A is a transverse cross-sectional diagram of catheter tip of the electrode of FIGS. 2A-B or 3A-B.

With reference to FIG. 4A, a cross sectional diagram 400 of a leading tip 410 (which may be similar to the tip 310) of an electrode (such as the electrode 210 of FIGS. 2A-B or 300 of FIGS. 3A-B). The diagram illustrates the structure of the leading tip 410 that includes the wide portions 412a-b, having a length of W, that are wider than the maximum width of the rest of the elongated body (whose end area, at the leading tip 410, is marked as end 414). The leading tip 410 also includes the opening 426 of a cannulation channel. As noted the cannulation channel tapers or narrows at an area proximate to the leading tip to allow irrigation fluid delivered through the cannulation channel extending along the elongated body (as illustrated by the cannulation channel 240 of FIG. 2) to be dispensed to the area being traversed by the electrode (e.g., as it is being guided via actuation of the catheter or guidewire), while preventing or inhibiting the catheter/guidewire (which has a diameter larger than the diameter of at least the opening 426) from being protruded or extending via the opening 426. The diagram 400 further shows a side of the nearest electrode contact 430 (i.e., nearest to the leading tip) disposed on the contact surface of the elongated body. As shown, the thickness of the electrode, from the bottom surface of the electrode contact 430, to the non-contact surface of the elongated body 410 of the electrode is marked as d, (similar to the thickness of the electrode 210 of FIG. 2A).

FIG. 4B is a transverse cross-sectional diagram 450 of a body 460 (similar to the bodies 210 or 300) of an electrode (such as the electrodes depicted in FIGS. 2A-B and 3A-B). Thus, the cross-sectional diagram 450 illustrates the structure that would be seen if the elongated body was transversely cut (e.g., along the line B-B depicted in FIG. 2B), and viewed from the side towards the location of the cut. As shown, the cut section of the elongated body 460 includes a cannulation channel 470 defined within the body 460 (similarly to the cannulation channel 240 of FIG. 2B). Also shown in FIG. 4B is a side of an electrode contact 480 nearest to the location of the transverse cut depicted in FIG. 4B. For example, if the transverse cut shown in FIG. 4B was made in the elongated body 210 of FIGS. 2A-B at a location between the electrode contacts 330a and 330b, the electrode 480 would correspond to the electrode contact 330a (or 230a) when the transverse cut is being viewed in a direction towards the leading tip of the elongated body. Here too, the distance d, between the two arrows provided in FIG. 4B, corresponds to the thickness of the electrode from the bottom surface of the electrode contact 480 to the non-contact surface of the elongated body of the electrode.

Figure 7:
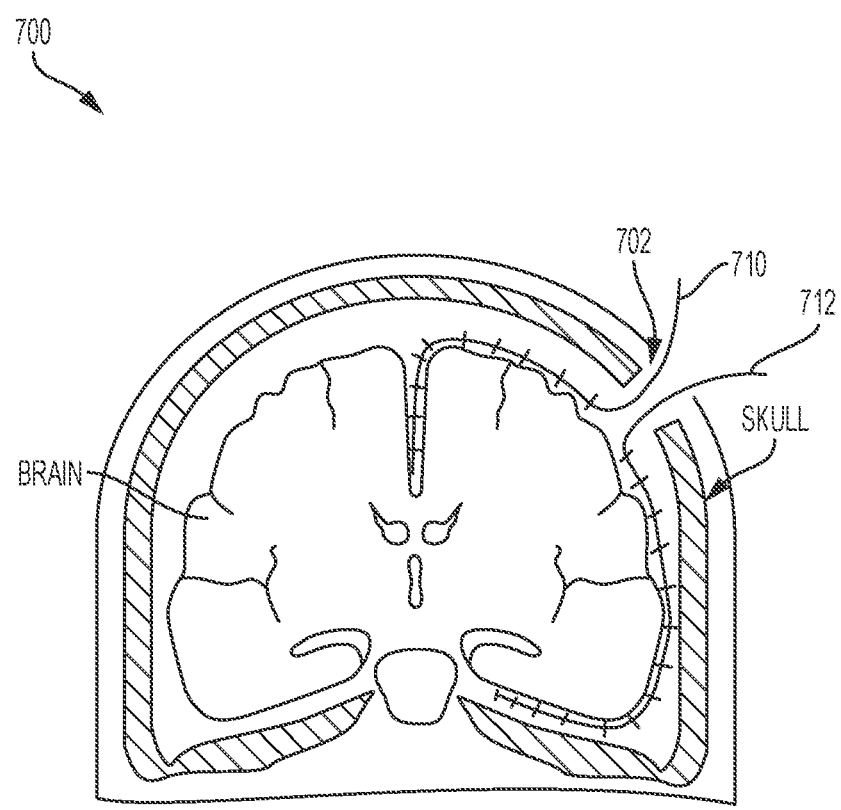
FIG. 7 is a diagram of electrodes, such as the electrodes of FIGS. 2A-4B, being placed in a subdural space of a patient's brain.

With reference next to FIG. 7, a diagram of an electrode array (comprising electrodes such as the electrodes of FIGS. 2A-5) placed in a subdural space of a patient's brain is shown. A guiding mechanism, such as a catheter or guidewire (such as the catheter/guidewire 250 of FIG. 2A, or the catheters/guidewires 510 and 610 of FIGS. 5 and 6) may be used to navigate the cannulated electrodes around angles distant from the entry point. The guiding mechanism used is fitted through cannulation channels of the respective electrodes, and guides (e.g., through actuation/manipulation of a controlling actuator of the guide mechanism) such electrodes through acute angles to their destination locations within the target area. Once a particular electrode has been placed at its destination, the catheter can be withdrawn (retracted) from the cannulation channel of that electrode, and fitted into another electrode, which is then guided, via the same bore hole 702 made in the skull (through which the previous electrode was guided to its destination) to the destination for the current electrode. In FIG. 7, electrodes 710 and 712 are shown making acute angles in the subdural space to allow coverage of the interhemispheric fissure and inferior brain surface.

More particularly, the process for placement of an electrode at hard-to-reach locations of the target array (e.g., the subdural space in the example of FIG. 7) is as follows. A 3-4 cm incision is generally made over the area of interest. A high-speed drill can be used to create a drill hole 15-20 mm in diameter. After hemostasis is obtained the dura is opened in a stellate fashion. A guide catheter is placed into an electrode and is carefully placed under the dural edge and advanced with the guide catheter while gently irrigating (as noted, the electrode being advanced may include multiple folded electrodes). The guiding catheter/guidewire is then removed, and is placed in the next electrode to be placed. This can be done with a large number of electrodes circumferentially around the drill hole. Intraoperative x-ray or fluoroscopy may be used to verify good placement. The leads are then tunneled out the skin surrounding the incision. The drill hole is then sealed with a polymer sealant such as Duraseal™ or a silastic burr hole cover so as to minimize the risk of cerebrospinal fluid leakage through the tunneling sites. Advantages of performing this procedure using the electrodes and devices described herein include the fact that a subdural array placed without craniotomy through a small drill hole would combine the favorable aspects of existing approaches, allowing good coverage of the cortex (where most seizures arise) while avoiding the invasiveness and risk of craniotomy. As noted, the approaches and devices (e.g., the cannulated subdural electrodes) described herein advantageously allow for use of a guide catheter whose tip can be molded into an appropriate angle to provide force tangential to the brain surface during placement. Also, the electrode is not pushed into position at its base but pulled into position by the catheter in the tip. Therefore, there is no need for the broad, flat design anywhere except the tip. The electrode can be narrow at the base, allowing for placement of an electrode array that can cover the brain in a radial fashion from one small drill hole. Other electrode deployment configurations (such as the configuration depicted in FIG. 7) may be realized. As noted, the guiding catheter/guidewire can also allow irrigation through perforations in the tip during placement to reduce the risk of brain injury. Molded catheters can not only help guide the electrode onto the brain surface initially, but also can help electrodes change direction intracranially. This aids in covering hard to access regions like the interhemispheric fissure and inferior brain surface.

Figure 8:
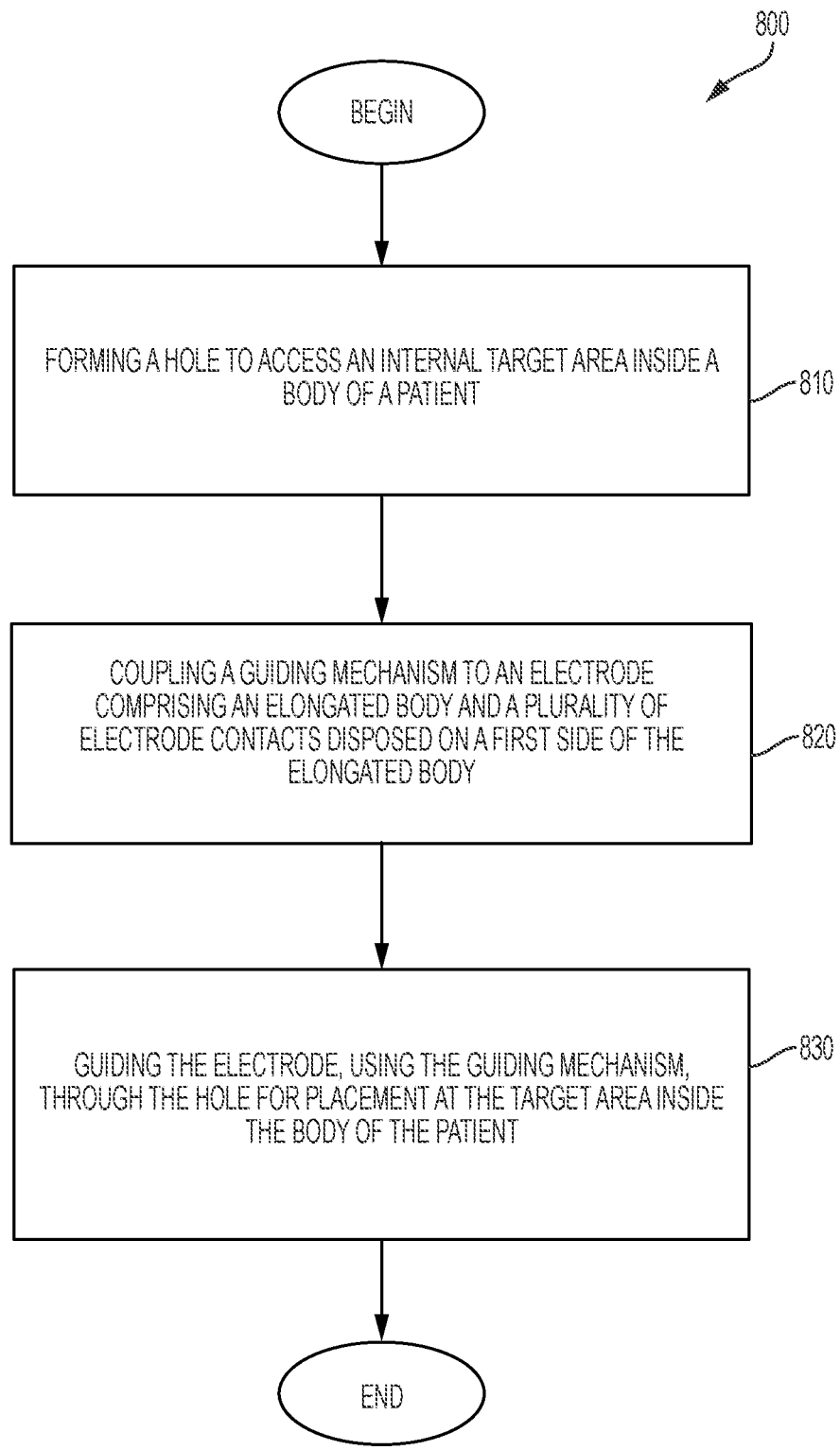
FIG. 8 is a flowchart of an example procedure to place electrodes.

With reference to FIG. 8, a flowchart of an example procedure 800 to place electrodes, such as the electrodes described herein, in a target area, is shown. The procedure 800 may be similar, at least in part, to the procedure described in relation to FIG. 7. The procedure 800 includes forming 810 a hole (e.g., a drill hole) to access an internal target area inside a body of a patient. For example, as discussed herein, when the electrode is to be deployed in the subdural space of the patient's brain, a high-speed drill may be used to create a drill hole 15-20 mm in diameter in the skull.

Having created the drill hole through which electrodes can be introduced (e.g., into the subdural space), the procedure 800 further includes coupling 820 a guiding mechanism (e.g., a catheter or guidewire, such as those schematically depicted in FIGS. 2A, 5, and 6) to an electrode (such as those discussed in relation to FIGS. 2A-4B) comprising an elongated body and a plurality of electrode contacts disposed on a first side of the elongated body. The electrode contacts may be rectangular or round in shape, and may be constructed from stainless steel, platinum, or some other conductive material. In some embodiments, coupling the guiding mechanism to the electrode may include inserting the guiding mechanism through a cannulation channel defined along a longitudinal axis of the elongated body of the electrode. Inserting the guiding mechanism through the cannulation channel may include one of, for example, inserting the guiding mechanism to the cannulation channel defined within the elongated body, or inserting the guiding mechanism to the cannulation channel defined in a sleeve disposed on a second side of the elongated body.

In some embodiments, and as was illustrated in FIGS. 3A-B, the elongated body may include a chain of body sections, with at least some of the body sections including tapered ends along a longitudinal axis of each of the at least some of the body sections, and with each of the plurality of electrode contacts being disposed at a respective different one of the body sections. In some examples, the elongated body may include a leading tip with an average width larger than a maximum body width of a remainder of the elongated body.

With continued reference to FIG. 8, the procedure 800 additionally includes guiding 830 the electrode, using the guiding mechanism (fitted through the cannulated channel), through the hole for placement at the target area inside the body of the patient. Guiding the electrode may be achieved through actuation of the guiding mechanism. For example, mechanical actuations may be applied through rotating and pushing of the catheter to cause the far end to likewise be rotated and pushed in such a way that the guiding mechanism, and thus the electrode, can negotiate sharp corners. In some embodiments, the operator's end of the of the guiding mechanism may have a specialized user interface (e.g., handle) that causes, through manipulation of that user interface, delivery of resultant electrical or mechanical power that causes other parts of the guiding mechanism (including the distal end of the guiding mechanism) to be actuated in some particular manner In some implementations, the procedure may also include, subsequent to placement of the electrode, repeating the coupling and guiding for one or more other electrodes for placement of the one or more other electrodes at respective one or more other locations. Thus, through repetition of this procedure, multiple electrodes can be fitted and passed through a single, and relatively small, drill hole. Furthermore, such electrodes can be guided to remote parts of the target area (e.g., locations at the opposite end of the head from where a drill hole was initially formed). In some embodiments, guiding the electrode may further include delivering irrigation fluid via the cannulation channel, with the irrigation fluids being dispensed through irrigation openings in the elongated body. For example, irrigating fluid (which may be introduced via an adapter, such as a luer-lock) may pass directly through the cannulation channel (e.g., in the space between the guiding mechanism and the internal walls of the cannulation channel), or indirectly through the cannulation channel (e.g., via an internal channel defined within the guiding mechanism that has been received in the cannulation channel). It is noted that the adapter may also be used to actuate the guiding mechanism to facilitate the advancement of the guiding mechanism and an electrode coupled thereto, to the destination location. Where the irrigation fluid passes through the guiding mechanism (such as a catheter), the guiding mechanism will include one or more perforations or openings (typical at the distal end of the guiding mechanism) through which the irrigation fluid can be delivered. That irrigation fluid is then dispensed through openings or perforations in the elongated body.

As noted, in some examples, the electrode may include multiple folded electrode strips defining the elongated body. In such embodiments, the procedure 800 may further include unfolding the multiple folded electrode strips defining the elongated body to deploy the unfolded electrode strips over the target area inside the body of the patient. The unfolding can be performed by actuating the guiding mechanism to cause rolling of the folded electrode strip to thus cause the strips to unfold and be deployed over the target area.

Figure 9:
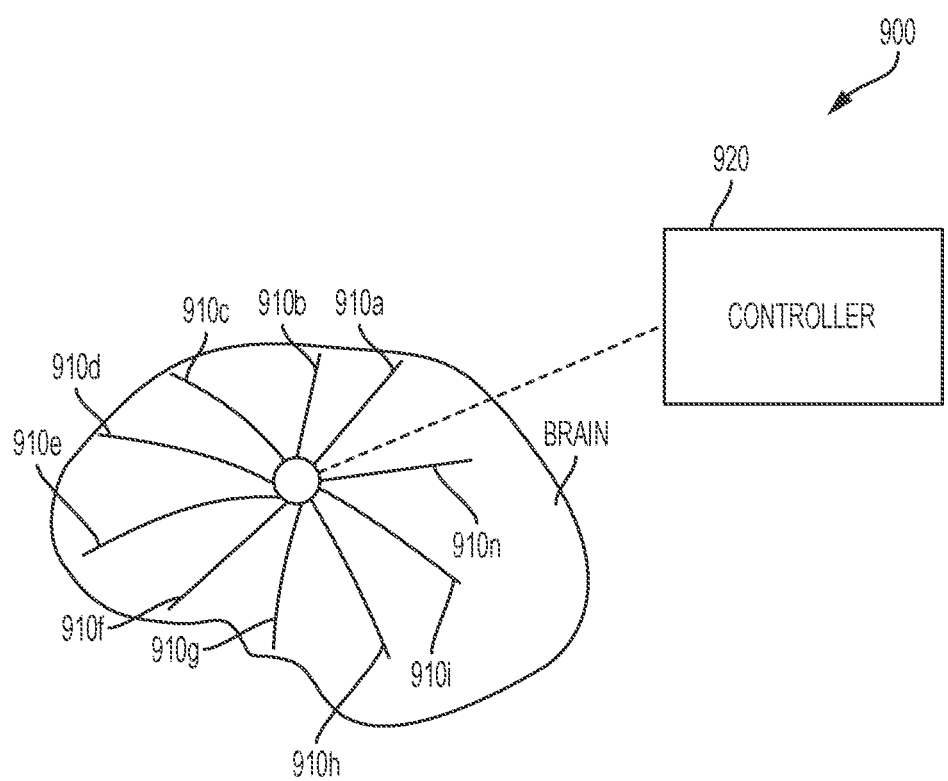
FIG. 9 is a diagram illustrating an example deployment of multiple electrodes.

Turning next to FIG. 9, a diagram 900 showing the resultant deployment of multiple electrodes 910a-n following performance of an electrode-placement procedure (such as the procedure 800 described in relation to FIG. 8) is provided. The placement of the multiple electrodes 910a-n can be achieved, in some embodiments, based on the narrow electrode profile that allows placement of multiple electrodes through a small skull opening. As illustrated in FIG. 9, the deployment of the multiple electrodes is based, in this example, on a radial scheme that is used to cover a large portion of the cerebral hemisphere using a small exposure. The particular deployment/distributive scheme that is used can be tailored to each individual patient, using, in each case, small exposure and multiple electrodes. Thus, any desired type of configuration (non-radial configuration, non-symmetrical configurations, etc.) may be used. The configuration used may be such where the electrodes are directed to various predetermined locations at the subdural space (or other locations within a body of a patient) for placement therein, with the tail end of the electrodes not necessarily being near the drill hole. That is, an electrode may be placed at a location where its tail end substantially far from the drill hole (and may be placed as far as the catheter, guidewire, or other guiding mechanism may reach inside the target area within the body of the patient). A controller 920 is in electrical communication with the electrode contacts on the multiple electrodes. Such electrical communication may be established, in some embodiments, via wired electrical connections, achieved using wires such as the wires 232a-n shown in FIG. 2B. Alternatively, the electrical communication between the controller 920 and the electrical contacts of the electrodes 910a-n can be performed using wireless communication, achieved using wireless transceivers included with the controller 920, and with the various electrical contacts disposed on the multiple electrodes (in some embodiments, one transceiver per electrode may be provided, with that transceiver then having direct electrical communication with the various electrode contacts on the respective electrode). The controller 920 is configured to collect measurements of electrical activities obtained through the electrode contacts, and/or to controllably send electrical signals (to cause electrical stimulation) to one or more of the electrode contacts. The controller 920 may also be configured to process signals it received, and/or communicate measurements it received to a remote device that performs further processing. In some embodiments, the controller 920 may be a processor-based controller, a state-machine controller, or any other type of controller. The controller 920 may also include a memory storage device to store data (e.g., measurement data collected from the various electrode contacts) and or programmable instructions to be executed on a processor, filtering circuitry (to filter or suppress signals that may cause adverse effects to the patient), a communication module (such as a transceiver), a power source (e.g., to operate the controller's circuitry, and/or to transmit electrical stimulation signals to various electrode contacts), and other circuits, modules, and components to operate the controller 920.

As noted, in some example embodiments, implementations in which a sound (or "probe") may first be placed at a target site, with a channeled electrode subsequently fitted on the sound for advancement to the target site, may be used. Such implementations avoid having to guide the bulkier combined assembly to the target site, which can be challenging to achieve when the path to the target site includes sharp turns and angles. Instead, only the lower profile and more flexible sound ("subdural guide" or "subdural sound") need be manipulated/guided through such irregular paths. Once this nimbler sound is in place, advancing the electrode on a rail (even if such a rail had to traverse similar sharp turns) becomes simpler. These implementations have the added advantage that the penetration distance (i.e., length of the path from the hole in the skull to the target site) can, relatively easily, be determined, thus allowing the right-sized electrode to be selected before the electrode is placed within the subdural space.

Figure 10A:
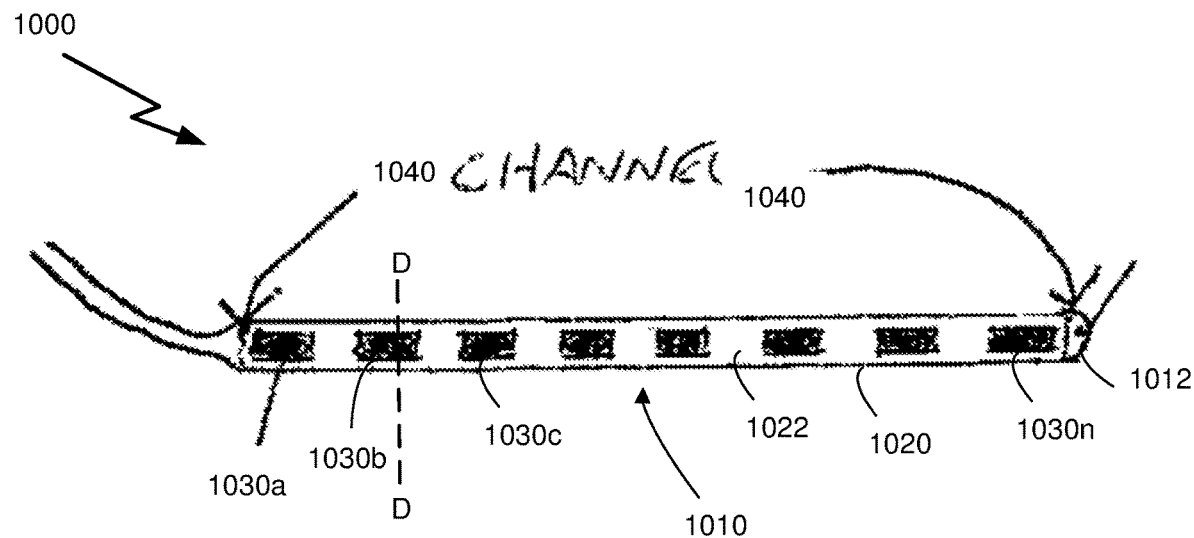
FIG. 10A is a bottom view of an example electrode configured to be used in conjunction with a subdural sound separately placed in a patient's subdural space.
Figure 10B:
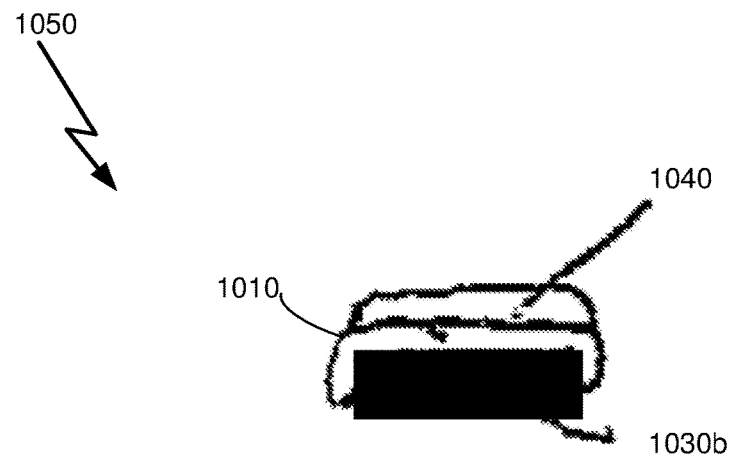
FIG. 10B is a cross-sectional view of the electrode of FIG. 10A.

Thus, with reference to FIG. 10A, a bottom view 1000 of an example electrode 1010 (also referred to as an "electrode array"), configured to be used in conjunction with a subdural sound (discussed in greater detail below) that is separately placed in a subdural space (e.g., of the brain area) of a patient, is shown. FIG. 10B is a cross-section view 1050 of the electrode 1010, illustrating the structure that would have been seen if the elongated body was transversely cut (e.g., along the line D-D depicted in FIG. 10A, which passes through the electrical contact 1030b), and viewed from the side towards the location of the cut. As shown in FIG. 10A, the electrode 1010 may include an elongated body 1020 with a first side 1022 that is substantially flat and is configured to be placed tangentially (and thereafter remain substantially in a fixed position) on the surface of the dura tissue of the patient. The elongated body 1020 of the electrode 1010 includes a plurality of electrical contacts 1030a-n (e.g., with n being 2, 3, 4, 8, or any other number of electrodes; generally, the number of contacts varies between 4-12) are disposed on the substantially flat first side 1022 of the elongated body and are configured to make physical contact with the target tissue (in this case the dura tissue). As shown in the cross-sectional view 1050 of FIG. 10B, in some embodiments, the electrical contacts may be placed within indentations or depressions defined on the flat side of the elongated body, with the contacts slightly protruding (extending) away from the side 1022 in order to establish adequate physical contact with the target surface. The electrical contacts 1030a-n may be manufactured from stainless-steel, platinum, or some other material with good electrical characteristics that satisfies signal measurement and/or electrical stimulation requirements.

Although not shown in FIGS. 10A or 10B, in some embodiments, extending from each of the electrical contacts 1030a-n is an electrical wire (similar to the implementations shown in relation to FIG. 2B) that can carry measured signals (representative of electrical activity within a brain, or of some other physiological activity in the target area where the electrode is deployed), and may also deliver electrical signals from an electrical source (e.g. a controller in communication with the various electrical contacts) to control the electrodes or to deliver electrical stimulation to the target area. In some embodiments, electrical signals may be communicated to and from the electrodes, or individually to and from the individual electrical contacts, via a wireless interface (e.g., a UHF-based transceiver, such as UHF transceivers implemented in passive RFID devices, to allow electrical operation of the devices using power harvested from wireless signals; such wireless transceivers may be configured to operate in other RF bands). In some examples, the electrical contacts 1030a-n may be rectangular contacts (or other electrode types and geometries) or have other shapes/configurations. The electrode 1010 may further include a radio-opaque identifier 1012 that allows for identification and tracking of the electrode 1010 using various imaging technologies (e.g., X-ray imaging). The electrode's wires may include unique color codes and/or may have unique radio-opaque identifiers.

As further shown in FIG. 10B, and similar to the electrodes 200 and 300 of FIGS. 2A-B and 3A-B, the electrode 1010 also includes a channel 1040 (referred to as a "soundage channel" because it is configured to receive a subdural sound/probe instrument) defined along the elongated body 1020 of the electrode 1010. The channel 1040 is located on or near the non-electrode contact surface and is generally narrow and oblate in order to accommodate a sound (guiding device) with a generally substantially flat shape. In some examples, the soundage channel 1040 may be defined within the elongated body 1020 (e.g., the elongated body 1020 may include an internal channel), whereas in some other examples, the soundage channel may be provided as the internal channel of a sleeve that is disposed on the electrode 1010 as a different part. The sleeve may be a non-integral part of the electrode, and may either be manufactured separately from the electrode on which the sleeve is disposed, or may be manufactured with the elongated body of the electrode (e.g., via extrusion molding manufacturing techniques). In the embodiments of the FIGS. 10A and 10B, the soundage channel (whether defined by a separate sleeve part, or defined as a channel within the elongated body 1020 of the electrode) is generally open at the two ends of the channel. The two-ended open configuration allows a sound, placed at an earlier time within the patient and extending from the entry site to the target site, to be fitted onto the leading end of the soundage channel (with the trailing end of the sound, located outside the patient's body, fitted into the leading end of the soundage channel), and to exit from the trailing end of the soundage channel. Once the soundage channel 1040 is fitted entirely onto the sound (so that separate sections of the sound extend from either of the two open ends of the soundage channel), the soundage channel 1040, and thus the rest of the electrode, can be advanced along the length of the sound until the electrode reaches the target tissue area proximate to the leading end of the sound, and be tangentially placed on the surface of the target tissue (e.g., the subdural tissue when the sound is configured as a subdural sound). The sound can be then withdrawn (pulled out) from the patient's body (e.g., from the trailing end of the soundage channel).

As further illustrated in FIG. 10B, the soundage channel 1040 may define an inner channel space that has a substantially rectangular cross-section, and which is thus structured to be fitted (snugly fitted, in some embodiments) on an elongated structure (constituting the body of the subdural sound) with a complementary rectangular cross section. As noted, creating a proper fit (e.g., a snug fit) between the rectangular cross-sectioned elongated structure of the sound and the complementary rectangular cross-sectioned soundage channel of the electrode allows for establishing sufficient traction between the inner walls of the soundage channel and the elongated structure of the subdural sound so as to help advance the soundage channel (and thus the electrode) along the subdural sound. The inner channel space of the soundage channel may be structured to have other cross-sectional shapes (e.g., circular, triangular, etc.), with the subdural sound typically structured to have a complementary shape that fits the shape of the soundage channel.

In some implementations, the elongated body of the electrode may be constructed as a chain of tapered sections, based on a structure similar to that depicted in FIGS. 3A and 3B (such tapering structure can increase flexibility of the electrode). Thus, in such implementations, the elongated body 1020 may include a chain of body sections, with at least some of the body sections including tapered ends along a longitudinal axis of electrode, with each of the plurality of electrical contacts being disposed at a respective different one of the body sections. Similarly to the electrodes 210 and 300, irrigation fluid can be delivered via an internal channel of the sound (the internal channel may be different than the soundage channel), or via the space defined between the internal walls of the soundage channel 1040 and the exterior of the sound fitted within the soundage channel 1040. Where the sound/probe includes an additional internal irrigation channel different from the soundage channel, such an additional irrigation channel may be open at the trailing end, and have a perforated end (near a leading tip of the elongated structure of the electrode) through which received irrigation fluid are dispensed. In some embodiments, the soundage channel 1040 may be tapered at the tip to allow passage of the irrigation fluid.

In some examples, the leading tip of the electrode may be the same width as the remainder of the electrode. An example value for the width is 3 mm, which allows placement of multiple (e.g., eight or more) electrodes through a small drill-hole. In some examples, rectangular electrical contacts approximately 2.75 mm×4.57 mm can be used to provide the same contact area as a standard 4 mm round electrode with a narrower profile. The electrical contacts can be spaced every 10 mm. In alternative embodiments, the spacing between contacts could vary. The electrode length can vary from 4 cm up to 16 cm, and possibly more. The soundage channel, in some examples, may be oblate in order to receive a substantially flat sound.

Figure 11:
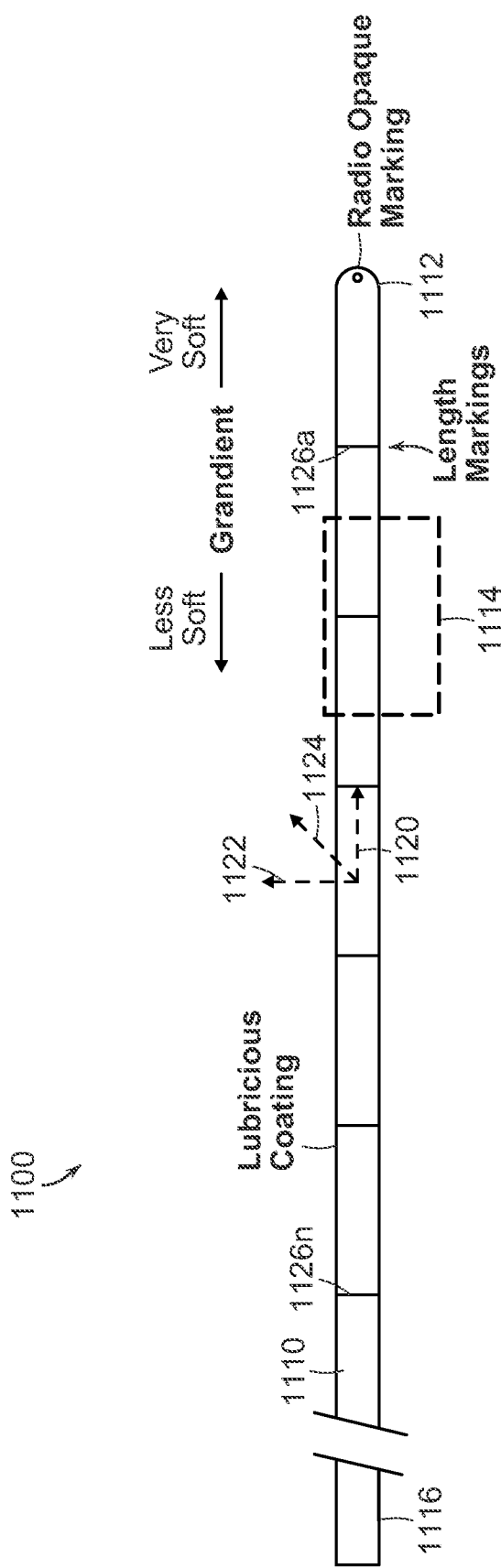
FIG. 11 is a top view of an example subdural sound configured to be placed at a target site and to then be received within a cannulation channel of, for example, the electrode of FIGS. 10A-B.

With reference next to FIG. 11, and with continued reference to FIGS. 10A-B, a top view of an example subdural sound 1100 (also referred to as a "subdural probe" or simply "probe"), configured to be placed at a target site (e.g., target tissue site within the subdural space of a patient's brain), and to then be received within a soundage channel of an electrode so that the electrode can advance (e.g., as on a rail) to the target site is shown. Typically, the subdural sound is initially guided to a target site within the cranial subdural space of the patient via a small opening in the skull and dura overlying the subdural space. The small profile and flexibility of the subdural sound allow easy navigation of the initial 90 degree angle under the skull into the subdural space and furthermore allow easy navigation of other angles encountered during navigation throughout the subdural space. The flat nature of the sound resists perpendicular deflection so it travels in the intended direction. In some implementations, the sound may be equipped with one or more optical fibers/wires that attach to a light-capture device (e.g., camera). A light source may deliver light signals via one such optical fibers, whose end is located near the leading end of the sound, to illuminate the area through which the sound is advancing, while another optical fiber optical wire may deliver reflected light back to the light-capture device, via a lens assembly, to allow the operator to view the area where the electrode is located. In other implementations, the sound is equipped with an electrical or chemical sensor at the tip that confirms the subdural location of the sound during navigation as the electrical and chemical properties of the subdural space differ from that of the brain.

The subdural sound 1100 includes an elongated subdural sound body 1110 which may include at least one substantially flat surface. In some such embodiments, such an elongated sound body may have a substantially rectangular cross section (and thus the sound's elongated structure will have four substantially flat surfaces) at different points along a longitudinal axis of the elongated structure. The sound is generally narrower than the electrode, and is structured to fit in the soundage channel of the electrode. The flatness (e.g., in the rectangular cross-sectional configuration) of the sound has been found to resist deflection of the sound from its intended trajectory in the subdural space, thus adding to the stability of the subdural sound as it is advanced through the patient's body en route to the destination target. As noted, the sound's structure (e.g., having a rectangular cross-section) may be such that it is configured to form a snug fit with the soundage channel of the electrode (e.g., in order to form good traction between the soundage channel). The sound may be manufactured using materials that allow a gradient of stiffness along the sound whereby it is more flexible at the leading aspect and relatively stiffer at the trailing aspect.

To facilitate advancement of the subdural sound to the target area (whether the sound is advanced on its own), and to also subsequently facilitate advancement of the soundage channel of the electrode on the deployed sound (acting as a rail), the elongated sound body 1110 may be a lubricious elongated structure. The lubricious characteristics of the elongated sound body may be achieved by coating the elongated structure of the sound with a low resistance or hydrophilic material. Such lubricious coating can minimize the sound's resistance to passage in the subdural space. Thus, where the subdural sound includes a lubricious elongated structure, when the electrode's soundage channel (e.g., the channel 1040 of FIG. 10B) is fitted on the trailing end (shown as the end 1116 in FIG. 11) of the elongated structure of the subdural sound (e.g., the elongated structure 1110 of the sound 1100 in FIG. 11), the electrode is configured to be advanced towards a leading end 1112 of the elongated structure of the subdural sound by operation of the soundage channel (e.g., 1040) sliding along the lubricious elongated body of the subdural sound. In some embodiments, the sliding motion can be achieved through manual sliding of the electrode along the sound's elongated structure (e.g., pushing or rolling the sleeve down a rail), or can be achieved through motorized actuation (e.g., a mechanism, not shown, that grasps the sound and pushes or pulls on it in order to achieve sliding motion towards the leading end of the subdural sound).

In some implementations, the elongated structure of the sound may be configured (e.g., through controlled manufacturing or construction) to have varying stiffness characteristics at different points along the elongated structure 1110. For example, the elongated structure 1110 of the sound 1100 may have a stiffness gradient such that the leading end 1112 of the elongated structure 1110 is more flexible than at least another portion (e.g., the portion marked as 1114, or the trailing end marked 1116) of the elongated structure. Such a stiffness profile makes the subdural sound flexible in directions parallel to the intended trajectory but stiff in directions perpendicular to the intended trajectory. A sound with such a stiffness gradient profile may be constructed by, for example, controlling the density of the material forming the subdural sound during the manufacturing process (e.g., during ejection of the material through an extrusion mold). Other potential methods to develop a stiffness gradient in the sound include laser cutting, blended extrusions, and stacked sections of variable durometer materials. In some examples, the sound may be configured to have stiffness characteristics (profile) that control the extent of deflection or swaying. For example, the sound's deflection (which may also be controllably configured through control of the material properties forming the subdural sound 1100) may be such that transverse (lateral) deflection (i.e., side-to-side deflection) is restricted/inhibited, while some up-and-down deflection (i.e., partial deflection along a normal axis 1124 that is normal to a longitudinal axis 1120 and a transverse axis 1122 depicted in FIG. 11) is allowed.

As further illustrated in FIG. 11, in some examples, the subdural sound 1100 may include a distance determination mechanism that is configured to indicate penetration distance of the subdural sound within the subdural space (or within the target tissue to which an electrode is to be advanced). By knowing the length/depth of the sound (e.g., as measured from the entry point into the body, to the leading point of the sound, proximate the target site), an electrode of an appropriate length (e.g., substantially equal to the determined length/depth of the sound) can be used, thus avoiding having to use an improperly sized electrode (which could result in having to fold or cut the excess length of the electrode, or snaking in a different electrode with a different length). In some examples, the distance determination mechanism may be realized as a plurality of markings 1126a-n disposed along the elongated structure 1110 of the subdural sound 1100 (the use of markings to indicate depth is reminiscent to marking used in a depth sound used to measure water depth). In some embodiments, one or more of the plurality of markings 1126a-n may include radio-opaque markings that can be detected and/or tracked using various imaging technologies (e.g., X-ray). In some embodiments, the subdural sound may be at least 20 cm in length, and may include a radio-opaque strip or filament throughout. The sound may be solid, but in some optional embodiments may include an irrigation channel (e.g., connected to a luer-lock and syringe) that allows for irrigation through a tip or along the entire electrode to lubricate passage.

In the operation, a 3-4 cm incision is made over the area of interest. A high speed drill is used to create a drill hole 15-20 mm in diameter. After hemostasis is obtained the dura is opened in a stellate fashion. The sound is then directed into the subdural space in the desired direction. The passage of the sound may be monitored with intra procedural x-ray, fluoroscopy, or any other imaging technology, as well as through tactile or in some embodiments visual or electro-chemical feedback. When the sound has reached the intended position, the appropriate length electrode is selected based upon the observed/determined length markings on the sound device. While care is taken that the sound is held still, the trailing end of the sound is then placed into the soundage channel at the leading tip of the electrode and the electrode is then advanced over the device to its final position in the subdural space. The sound is then withdrawn and the appropriate position of the electrode may be confirmed with x-ray or fluoroscopy. The same device and technique is then used to place additional electrodes until a desired electrode array is achieved. The leads are then tunneled out the skin surrounding the incision. The drill hole is then sealed with a polymer sealant such as Duraseal™ or a silastic burr hole cover so as to minimize the risk of cerebrospinal fluid leakage through the tunneling sites.

Figure 12:
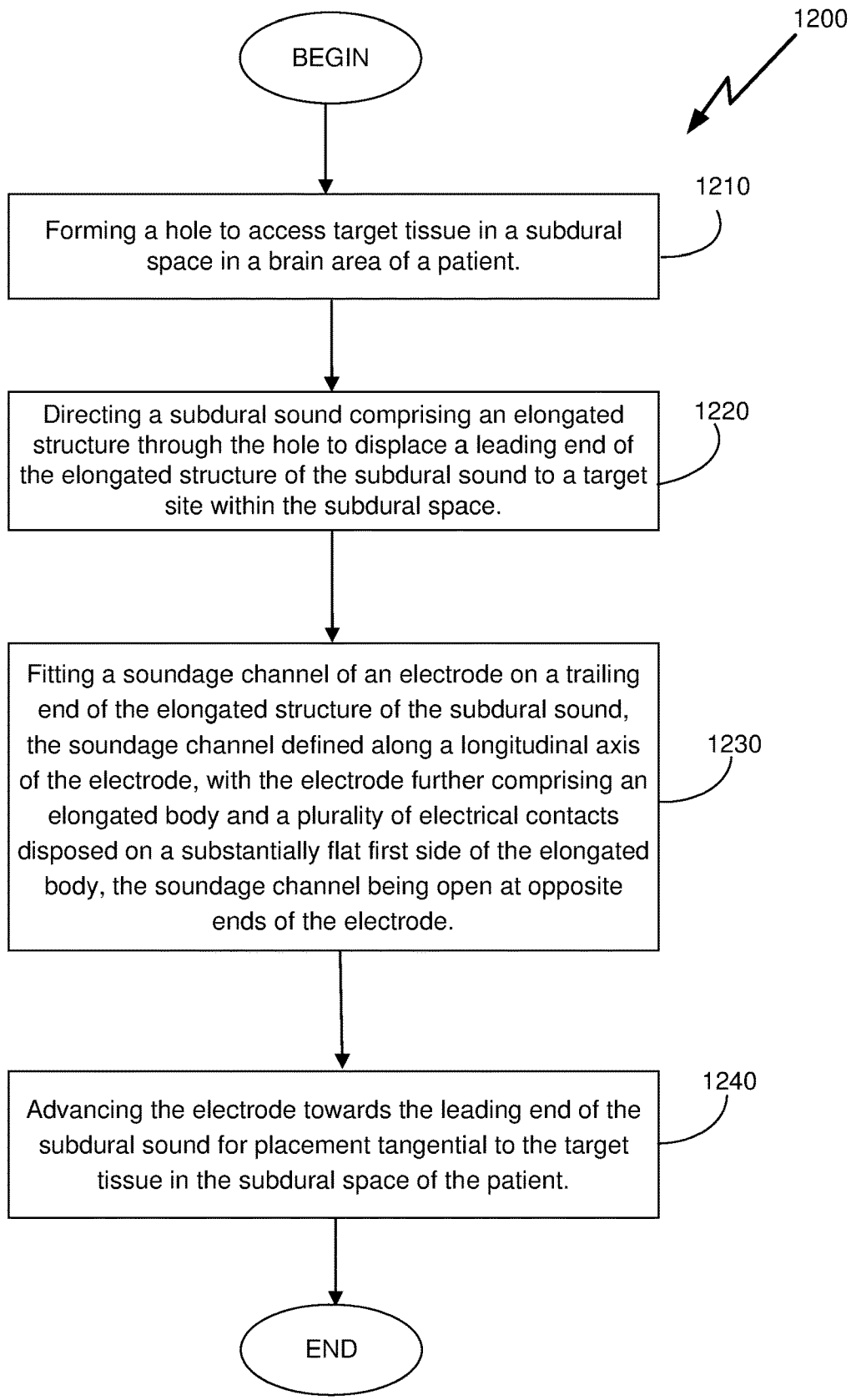
FIG. 12 is a flowchart of an example procedure for placement of an electrode using a subdural sound placed at a target tissue within a patient's subdural space.

More particularly, and with reference next to FIG. 12, a flowchart of a procedure 1200 for placement of electrode (such as the electrode 1010 shown in FIG. 10A), using a subdural sound (such as the sound 1100 depicted in FIG. 11) at a target tissue within the subdural space (e.g., of the brain) of a patient, is shown. The procedure 1200 is also described with further reference to FIG. 13, providing a diagram 1300 showing a system, comprising an electrode and a subdural sound, in operation.

The procedure 1200 includes forming 1210 a hole (such as the hole 1310 shown in FIG. 13) to access target tissue (namely, tissue 1320 in FIG. 13) in a subdural space of a patient. Having formed an accessed hole, the procedure 1200 additionally includes directing 1220 a subdural sound (such as a subdural sound 1330 in FIG. 13, or the subdural sound 1100 illustrated in FIG. 11) comprising an elongated structure through the hole to displace a leading end of the elongated structure of the subdural sound to a target site (e.g., near the target tissue 1320 in FIG. 13) within the subdural space. As noted, in some embodiments, directing the sound to the target site may be done manually (e.g., the surgeon pushing the sound, possibly based on image data obtained using a fiber optic arrangement coupled to the subdural sound), or may be done with the aid of another tool. The subdural sound may include an elongated structure (e.g., a lubricious elongated structure, which optionally may have a stiffness profile in which a leading end of the sound is more flexible than some other portion of the sound) with at least one substantially flat surface. In some examples, the elongated structure of the sound may have a substantially rectangular cross section at points along a longitudinal axis (e.g., the axis 1120 shown in FIG. 11) of the elongated structure of the subdural sound.

Figure 13:
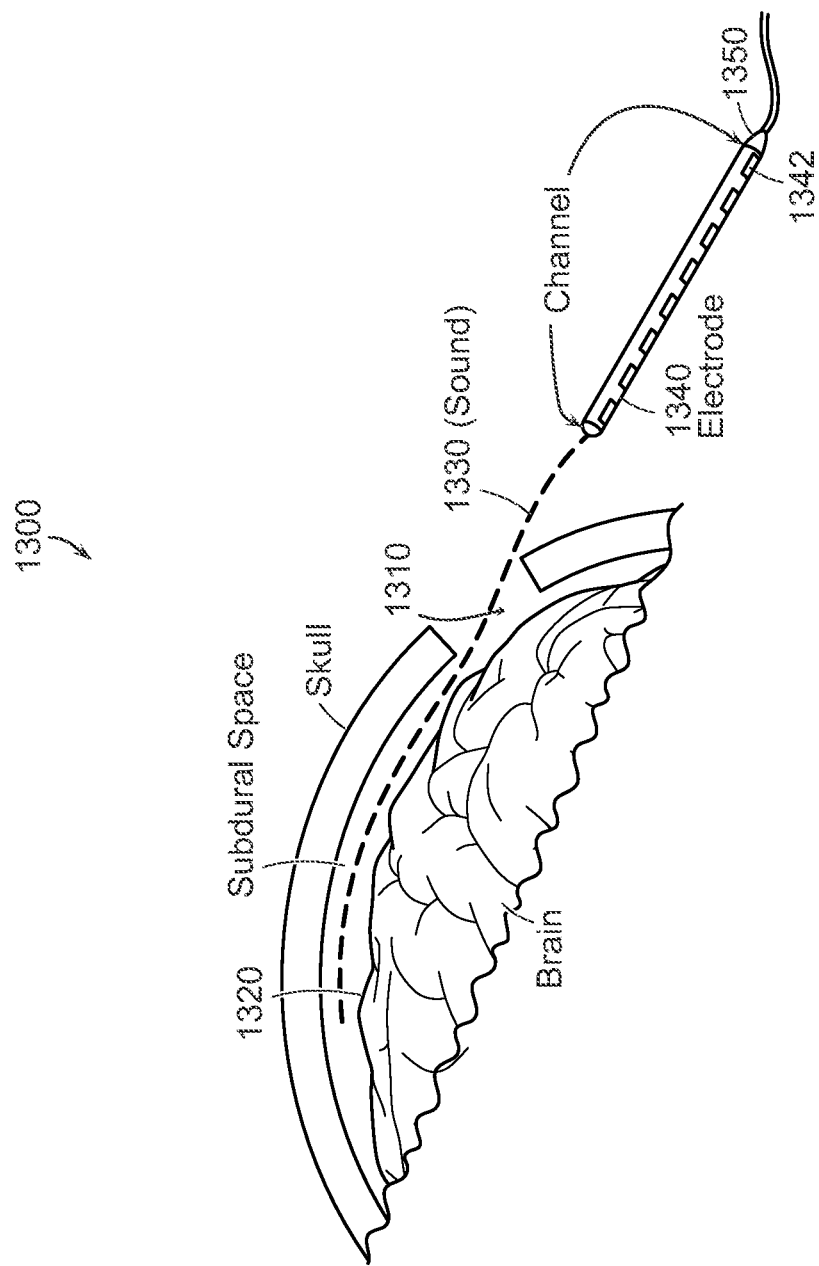
FIG. 13 is diagram showing a system comprising an electrode and a subdural sound in operation.

With continued reference to FIG. 12, the procedure 1200 further includes fitting 1230 a soundage channel (one such soundage channel may be the channel with the opening 1350 illustrated in FIG. 13) of an electrode (such as the electrode 1340 of FIG. 13, the electrode 1010 of FIG. 10A, or any of the other electrodes depicted and discussed in the present disclosure) on a trailing end of the elongated structure of the subdural sound, with the soundage channel defined along a longitudinal axis of the electrode, with the electrode further comprising an elongated body and a plurality of electrical contacts (such as the contact 1342) disposed on a substantially flat first side of the elongated body, and with the soundage channel being open at opposite ends. As noted, in some examples, the soundage channel defines an inner channel space with a substantially rectangular cross section. In such examples, fitting the soundage channel on the trailing end of the elongated structure of the subdural sound may include snugly fitting the soundage channel (with the substantially rectangular cross section) on the elongated structure (of the subdural sound) that has a substantially rectangular cross section.

As noted, in some embodiments, the subdural sound may further include a distance determination mechanism configured to indicate a penetration distance of the subdural sound into the subdural space. Thus, in such examples, fitting the soundage channel on the trailing end of the elongated structure of the subdural sound may include determining penetration distance of the subdural sound into the subdural space based on markings disposed on the elongated structure of the subdural sound, and fitting one of a plurality of available electrodes with a length selected based on the determined penetration distance. In other words, the markings visible on the subdural sound can indicate how far into the tissue the sound has been guided. Based on that distance, an electrode is selected from an available inventory of electrodes, with the selected electrode having an electrode length matching (or nearly matching) the distance indicated by the markings on the sound.

In some implementations, fitting the soundage channel on the trailing end of the elongated structure of the subdural sound may include fitting the trailing end of the elongated structure of the subdural sound within the soundage channel defined in the elongated body of the electrode, or fitting the trailing end of the elongated structure of the subdural sound within the soundage channel defined in a sleeve disposed on a second side of the elongated body of the electrode.

With continued reference to FIG. 12, the procedure 1200 also includes advancing 1240 the electrode towards the leading end of the subdural sound for placement tangential to the target tissue in the subdural space of the patient. As noted, advancing the electrode can be performed by manually pushing (sliding) the electrode, whose soundage channel has been fitted onto the elongated structure of the subdural sound, along the length of the elongated structure. Alternatively, a displacement mechanism within the soundage channel (which potentially can be actuated by an external or internal motor) can cause displacement of the electrode along the subdural sound.

In some examples, the elongated structure of the subdural sound may include an elongated sound body with stiffness characteristics that restrict transverse deflection of the elongated sound body along a transverse axis of the elongated body (e.g., the axis 1122 of FIG. 11), the stiffness characteristics of the elongated sound body further configured to allow partial deflection along a normal axis (e.g., the axis 1124) that is normal to the transverse axis and a longitudinal axis of the elongated body. In some embodiments, the procedure 1200 may further include withdrawing the subdural sound subsequent to placement of the electrode, and repeating the directing (1220), fitting (1230), and advancing (1240) for one or more other subdural sounds and/or for one or more electrodes, at respective one or more locations in the subdural space. In some embodiments, the procedure 1200 may further include delivering irrigation fluid via the soundage channel. Alternatively, in some examples, the procedure 1200 may further include delivering irrigation fluid via an irrigation channel, different from the soundage channel, configured to receive irrigation fluids dispensed through a perforated end of the irrigation channel located near a leading tip of the elongated structure of the electrode.

In some additional examples, the electrode may include multiple folded electrode strips defining the elongated body, and the procedure 1200 may then further include unfolding the multiple folded electrode strips defining the elongated body to deploy the unfolded electrode strips over the target tissue.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

What is claimed is:

1. A system comprising:
   a subdural sound comprising an elongated structure configured to be placed within a subdural space of a brain area of a patient; and
   an electrode comprising an elongated body, a plurality of electrical contacts disposed on a substantially flat first side of the elongated body, and a soundage channel defined along a longitudinal axis of the electrode and open at opposite ends, wherein the soundage channel at the leading end of the electrode is fitted on the trailing end of the elongated structure of the subdural sound, after the subdural sound is placed within the subdural space at a target site, so as to be advanced to the target site in the subdural space for tangential placement of the electrode on target tissue in the subdural space of the brain area.

2. The system of claim 1, wherein the subdural sound comprises the elongated structure with at least one substantially flat surface.

3. The system of claim 2, wherein the sound has a substantially rectangular cross section at points along a longitudinal axis of the elongated structure of the sound.

4. The system of claim 3, wherein the soundage channel of the electrode defines an inner channel space, with a substantially rectangular cross section, to be snugly fitted on the elongated structure of the subdural sound having the substantially rectangular cross section.

5. The system of claim 1, wherein the subdural sound further comprises a distance determination mechanism configured to indicate penetration distance of the subdural sound into the subdural space.

6. The system of claim 5, wherein the distance determination mechanism comprises a plurality of markings disposed along the elongated structure to indicate the penetration distance of the subdural sound.

7. The system of claim 6, wherein the plurality of markings comprise radiopaque markings.

8. The system of claim 1, wherein the elongated structure of the subdural sound includes a body with stiffness gradient such that a leading end of the elongated structure is more flexible than at least another portion of the body.

9. The system of claim 1, wherein the elongated structure of the subdural sound includes an elongated sound body with stiffness characteristics that restrict transverse deflection of the body along a transverse axis of the elongated sound body, the stiffness characteristics of the elongated sound body further configured to allow partial deflection along a normal axis that is normal to the transverse axis and a longitudinal axis of the elongated sound body.

10. The system of claim 1, wherein the soundage channel is defined within the elongated body of the electrode.

11. The system of claim 1, wherein the elongated body of the electrode comprises a chain of body sections, wherein at least some of the body sections include tapered ends along a longitudinal axis of each of the at least some of the body sections, and wherein each of the plurality of electrical contacts is disposed at a respective different one of the body sections.

12. The system of claim 1, wherein the elongated structure of the subdural sound includes a lubricious elongated sound body, and wherein the electrode soundage channel fitted on the trailing end of the elongated structure of the subdural sound is configured to be advanced towards a leading end of the elongated structure of the subdural sound by sliding along the lubricious elongated sound body of the subdural sound.

13. The system of claim 1, further comprising an adapter fitted at one of an operator-end of the subdural sound or a trailing opening of the soundage channel, the adapter configured to at least direct irrigation fluids from a fluid source for delivery via the soundage channel.

14. The system of claim 1, wherein each of the plurality of electrical contacts comprises one or more of: a stainless-steel contact, or a platinum contact.

15. The system of claim 1, wherein the electrode comprises multiple folded electrode strips defining the elongated body, the multiple folded electrode strip configured to be unfolded for deployment over the target tissue in the subdural space.

16. The system of claim 1, wherein the sound further includes an irrigation channel, different from the soundage channel, configured to receive irrigation fluids dispensed through a perforated end located near a leading tip of the elongated structure of the electrode.

17. The method of claim 1, further comprising:
delivering irrigation fluid via an irrigation channel, different from the soundage channel, configured to receive irrigation fluids dispensed through a perforated end of the irrigation channel located near a leading tip of the elongated structure of the electrode.

18. A method comprising:
forming a hole to access target tissue in a subdural space in a brain area of a patient;
directing a subdural sound comprising an elongated structure through the hole to displace a leading end of the elongated structure of the subdural sound to a target site within the subdural space;
fitting, after the subdural sound is placed within the subdural space at the target site, a soundage channel of an electrode on a trailing end of the elongated structure of the subdural sound, the soundage channel defined along a longitudinal axis of the electrode, with the electrode further comprising an elongated body and a plurality of electrical contacts disposed on a substantially flat first side of the elongated body, the soundage channel being open at opposite ends of the electrode; and
advancing the electrode towards the leading end of the subdural sound for placement tangential of the electrode on the target tissue in the subdural space of the patient.

19. The method of claim 18, wherein the subdural sound comprises an elongated structure with at least one substantially flat surface, and having a substantially rectangular cross section at points along a longitudinal axis of the elongated structure of the subdural sound.

20. The method of claim 19, wherein the soundage channel defines an inner channel space with a substantially rectangular cross section, and wherein fitting the soundage channel on the trailing end of the elongated structure of the subdural sound comprises snugly fitting the soundage channel, with the substantially rectangular cross section, on the elongated structure with the substantially rectangular cross section.

21. The method of claim 18, wherein the subdural sound further comprises a distance determination mechanism configured to indicate a penetration distance of the subdural sound into the subdural space.

22. The method of claim 21, wherein fitting the soundage channel on the trailing end of the elongated structure of the subdural sound comprises:
determining penetration distance of the subdural sound into the subdural space based on markings disposed on the elongated structure of the subdural sound; and
fitting one of a plurality of available electrodes with a length selected based on the determined penetration distance.

23. The method of claim 18, wherein the elongated structure of the subdural sound includes an elongated sound body with stiffness characteristics that restrict transverse deflection of the elongated sound body along a transverse axis of the elongated sound body, the stiffness characteristics of the elongated sound body further configured to allow partial deflection along a normal axis that is normal to the transverse axis and a longitudinal axis of the elongated sound body.

24. The method of claim 18, wherein fitting the soundage channel on the trailing end of the elongated structure of the subdural sound comprises:
fitting the trailing end of the elongated structure of the subdural sound within the soundage channel defined in the elongated body of the electrode, or fitting the trailing end of the elongated structure of the subdural sound within the soundage channel defined in a sleeve disposed on a second side of the elongated body of the electrode.

25. The method of claim 18, further comprising:
withdrawing, subsequent to placement of the electrode, the subdural sound; and
repeating the directing, fitting, and advancing for one or more other subdural sounds and for one or more electrodes, at respective one or more locations in the subdural space.

26. The method of claim 18, further comprising:
delivering irrigation fluid via the soundage channel.

27. The method of claim 18, wherein the electrode comprises multiple folded electrode strips defining the elongated body, and wherein the method further comprises:
unfolding the multiple folded electrode strips defining the elongated body to deploy the unfolded electrode strips over the target tissue.

28. An electrode comprising:
an elongated body;
a plurality of electrode contacts disposed on a substantially flat first side of the elongated body; and
a soundage channel defined along a longitudinal axis of the elongated body and open at opposite ends, the soundage channel configured to be fitted on a trailing end of an elongated structure of a subdural sound after the subdural sound is placed within the subdural space at a target site in order to advance the electrode for tangential placement on target tissue in the subdural space of a brain area of a patient.

29. The electrode of claim 28, wherein the soundage channel is defined within one of: the elongated body, or a sleeve disposed on a second side of the elongated body of the electrode.

30. The electrode of claim 28, wherein the elongated body comprises a chain of body sections, wherein at least some of the body sections include tapered ends along a longitudinal axis of each of the at least some of the body sections, and wherein each of the plurality of electrical contacts is disposed at a respective different one of the body sections.

31. The electrode of claim 28, further comprising:
multiple folded electrode strips defining the elongated body, the multiple folded electrode strips configured to be unfolded for deployment over the target area inside the body of the patient.

32. The electrode of claim 28, wherein the soundage channel defines a substantially rectangular cross section, at points along a longitudinal axis of the soundage channel, snugly fittable on a trailing end of the elongated structure of the subdural sound, having a corresponding substantially rectangular cross section at points along a longitudinal axis of the elongated structure of the subdural sound, when the elongated structure of the subdural sound is placed within the subdural space of the patient.

33. A system comprising:
a subdural sound comprising an elongated structure configured to be placed within a subdural space of a brain area of a patient;
an electrode comprising an elongated body, a plurality of electrical contacts disposed on a substantially flat first side of the elongated body, and a soundage channel defined along a longitudinal axis of the electrode and open at opposite ends, wherein the soundage channel at the leading end of the electrode is fitted on the trailing end of the elongated structure of the subdural sound so as to be advanced, when the subdural sound is placed within the subdural space, to a target site in the subdural space for tangential placement on target tissue in the subdural space of the brain area; and
a sleeve disposed on a second side of the elongated body of the electrode, wherein the soundage channel is defined by the sleeve.

34. The system of claim 33, wherein the subdural sound comprises the elongated structure with at least one substantially flat surface.

35. The system of claim 34, wherein the sound has a substantially rectangular cross section at points along a longitudinal axis of the elongated structure of the sound, and wherein the soundage channel of the electrode defines an inner channel space, with a substantially rectangular cross section, to be snugly fitted on the elongated structure of the subdural sound having the substantially rectangular cross section.

36. The system of claim 33, wherein the elongated structure of the subdural sound includes a body with stiffness gradient such that a leading end of the elongated structure is more flexible than at least another portion of the body.

37. The system of claim 33, wherein the elongated structure of the subdural sound includes an elongated sound body with stiffness characteristics that restrict transverse deflection of the body along a transverse axis of the elongated sound body, the stiffness characteristics of the elongated sound body further configured to allow partial deflection along a normal axis that is normal to the transverse axis and a longitudinal axis of the elongated sound body.

38. The system of claim 33, further comprising an adapter fitted at one of an operator-end of the subdural sound or a trailing opening of the soundage channel, the adapter configured to at least direct irrigation fluids from a fluid source for delivery via the soundage channel.

* * * * *